(12) United States Patent
    Daniels

(10) Patent No.: US 9,390,630 B2
(45) Date of Patent: Jul. 12, 2016

(54) ACCELERATED LEARNING, ENTERTAINMENT AND COGNITIVE THERAPY USING AUGMENTED REALITY COMPRISING COMBINED HAPTIC, AUDITORY, AND VISUAL STIMULATION

(71) Applicant: John James Daniels, Madison, CT (US)

(72) Inventor: John James Daniels, Madison, CT (US)

( * ) Notice: Subject to any disclaimer, the term of this patent is extended or adjusted under 35 U.S.C. 154(b) by 0 days.

(21) Appl. No.: 14/269,133

(22) Filed: May 3, 2014

(65) Prior Publication Data

US 2015/0317910 A1    Nov. 5, 2015

Related U.S. Application Data

(60) Provisional application No. 61/818,971, filed on May 3, 2013.

(51) Int. Cl.
    *G09B 15/00* (2006.01)
    *A61M 21/00* (2006.01)
    *G09B 9/00* (2006.01)
    (Continued)

(52) U.S. Cl.
    CPC .............. *G09B 15/00* (2013.01); *A61M 21/00* (2013.01); *G09B 5/065* (2013.01); *G09B 9/00* (2013.01); *G09B 9/003* (2013.01); *G09B 9/063* (2013.01); *G09B 9/08* (2013.01); *G09B 9/52* (2013.01); *G09B 19/00* (2013.01); *G09B 19/0038* (2013.01); *G09B 19/22* (2013.01); *G10H 1/18* (2013.01); *A61M 2021/005* (2013.01); *A61M 2021/0016* (2013.01); *A61M 2021/0022* (2013.01); *A61M 2021/0027* (2013.01); *A61M 2021/0072* (2013.01); *A61M 2021/0077* (2013.01); *A61M 2205/507* (2013.01); *A61M 2210/0612* (2013.01);

(Continued)

(58) Field of Classification Search
    CPC ....................................................... G10H 1/18
    USPC .................................................... 84/615, 653
    See application file for complete search history.

(56) References Cited

U.S. PATENT DOCUMENTS

6,411,276 B1 * 6/2002 Braun ................... G05G 9/047
                                                          345/156
8,378,964 B2 * 2/2013 Ullrich .................... G08B 6/00
                                                          345/156

(Continued)

*Primary Examiner* — David Warren
(74) *Attorney, Agent, or Firm* — John James Daniels

(57) ABSTRACT

An accelerated learning and rehabilitation system for teaching the performance of a musical instrument, a remotely operated system, a sport, a weapon, and for brain rehabilitation and other uses includes generating sensory cues including auditory, haptic and visual sensory cues capable of being perceived by a user. The generated sensory cues are applied to the user and are dependent on a position of at least one body member of a performer relative to a performance element of a performance object with which an event is performed. The sensory cues are effective for stimulating a various processing center of a brain of the user so that user learns how to position his body member corresponding to the position of the performer of the event. The sensory cues can include visual sensory cues effective for stimulating the visual processing center of the brain of the user. The visual sensory cues are synchronized with the other applied sensory cues so that the position of the body member of the performer is virtually visually indicated in synchronization with the other sensory cues so that the visual processing center is stimulated with a visual sensory cue in synchronization with the stimulation of other processing centers corresponding to the other sensory cues for teaching the user to perform a version of the event.

20 Claims, 24 Drawing Sheets

(51) Int. Cl.
  *G09B 19/00*  (2006.01)
  *G09B 9/52*  (2006.01)
  *G09B 9/08*  (2006.01)
  *G09B 9/06*  (2006.01)
  *G09B 5/06*  (2006.01)
  *G09B 19/22*  (2006.01)
  *G10H 1/18*  (2006.01)

(52) U.S. Cl.
  CPC . *A61M 2210/0662* (2013.01); *A61M 2210/083* (2013.01); *A61M 2210/086* (2013.01)

(56) References Cited

U.S. PATENT DOCUMENTS

| | | | | |
|---|---|---|---|---|
| 8,552,847 | B1* | 10/2013 | Hill | G06F 3/016 116/205 |
| 2003/0068053 | A1* | 4/2003 | Chu | G06F 3/016 381/118 |
| 2003/0170602 | A1* | 9/2003 | Hagita | G09B 5/00 434/307 R |
| 2004/0174431 | A1* | 9/2004 | Stienstra | G06F 3/011 348/155 |
| 2007/0000374 | A1* | 1/2007 | Clark | G10H 1/0008 84/724 |
| 2007/0282228 | A1* | 12/2007 | Einav | A61B 5/7475 601/33 |
| 2009/0053683 | A1* | 2/2009 | Brown | G09B 23/32 434/272 |
| 2009/0231276 | A1* | 9/2009 | Ullrich | G06F 3/016 345/157 |
| 2011/0048213 | A1* | 3/2011 | Choi | G10G 1/00 84/461 |
| 2011/0238079 | A1* | 9/2011 | Hannaford | A61B 19/2203 606/130 |
| 2012/0094263 | A1* | 4/2012 | Seitz | G09B 5/06 434/307 R |
| 2012/0216666 | A1* | 8/2012 | Fresolone | G09B 21/009 84/483.2 |
| 2012/0260789 | A1* | 10/2012 | Ur | G09B 19/0038 84/470 R |
| 2013/0029791 | A1* | 1/2013 | Rose | G09B 19/0038 473/409 |
| 2013/0118339 | A1* | 5/2013 | Lee | G10H 1/32 84/725 |
| 2013/0207890 | A1* | 8/2013 | Young | A63F 13/06 345/156 |
| 2013/0310122 | A1* | 11/2013 | Piccionielli | G07F 17/3272 463/2 |
| 2014/0038139 | A1* | 2/2014 | AlDossary | G09B 21/001 434/114 |
| 2014/0186810 | A1* | 7/2014 | Falash | G09B 7/00 434/308 |
| 2014/0248594 | A1* | 9/2014 | Navas | A61B 5/1124 434/247 |
| 2014/0282105 | A1* | 9/2014 | Nordstrom | H04L 65/403 715/753 |
| 2015/0050623 | A1* | 2/2015 | Falash | G09B 9/24 434/38 |
| 2015/0140528 | A1* | 5/2015 | Sikstrom | A61B 5/16 434/236 |
| 2015/0140529 | A1* | 5/2015 | Tinjust | A61B 5/16 434/236 |
| 2015/0221230 | A1* | 8/2015 | Karadjian | G09B 9/00 434/353 |
| 2015/0269863 | A1* | 9/2015 | Shrewsbury | G09B 11/00 434/162 |
| 2015/0279238 | A1* | 10/2015 | Forte | G09B 7/02 434/271 |
| 2015/0294585 | A1* | 10/2015 | Kullok | A61B 5/743 434/236 |
| 2015/0294597 | A1* | 10/2015 | Rizzo | A61H 3/04 340/4.12 |
| 2015/0302763 | A1* | 10/2015 | Gleim | G09B 9/00 434/237 |
| 2015/0314195 | A1* | 11/2015 | Bekri | A63F 13/285 463/30 |
| 2015/0317910 | A1* | 11/2015 | Daniels | G09B 15/00 84/485 R |
| 2015/0323993 | A1* | 11/2015 | Levesque | G06F 3/016 345/156 |

* cited by examiner

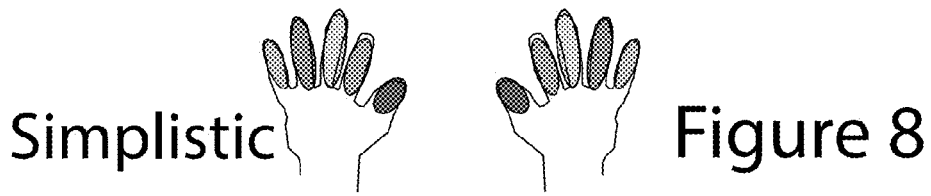
Simplistic     Figure 8
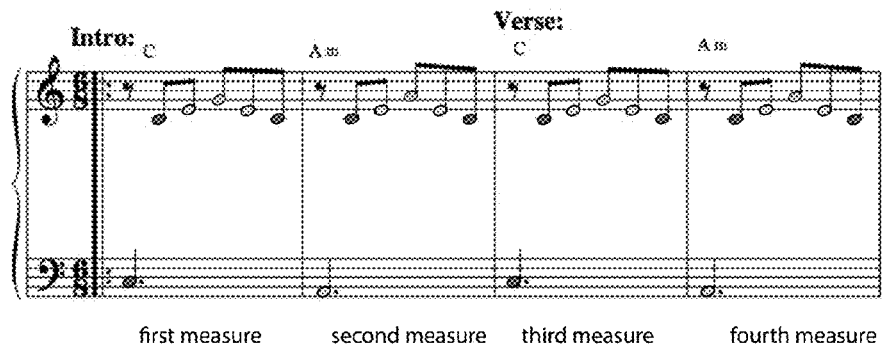
first measure    second measure    third measure    fourth measure
Figure 9
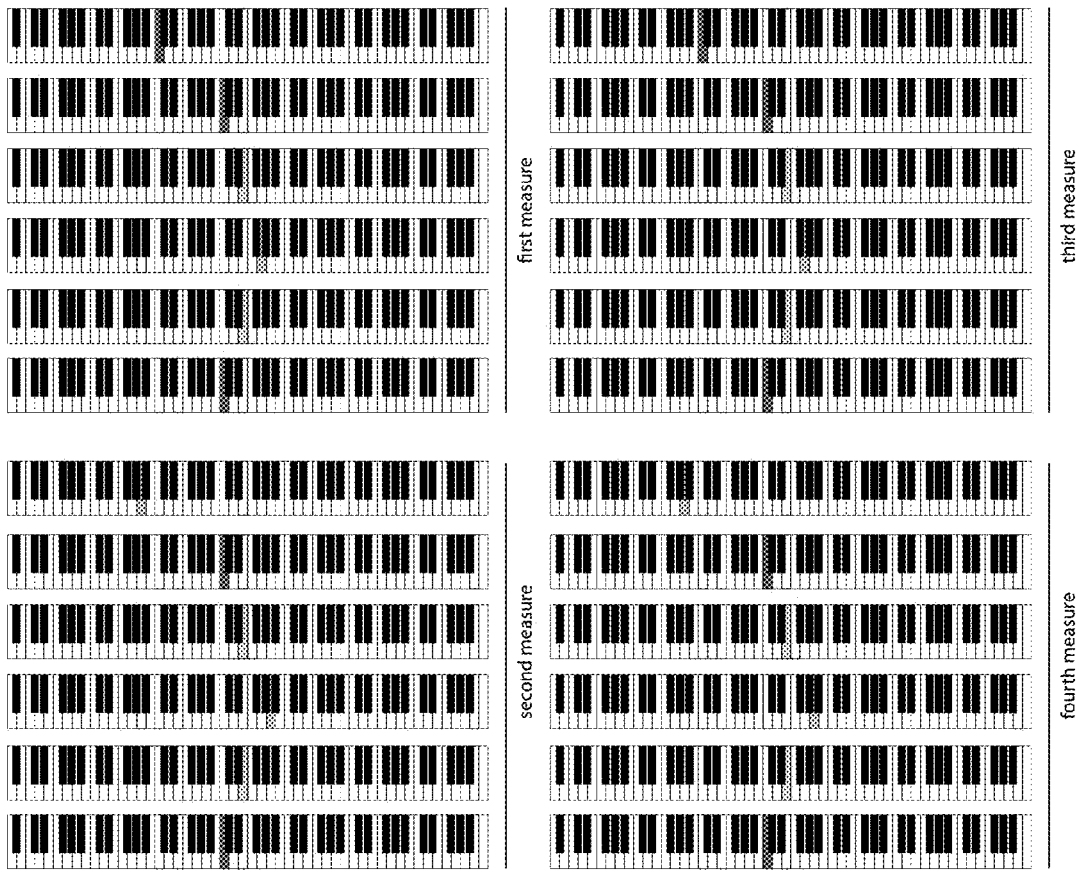
Figure 10

Full Chords first measure　　second measure　third measure　　fourth measure

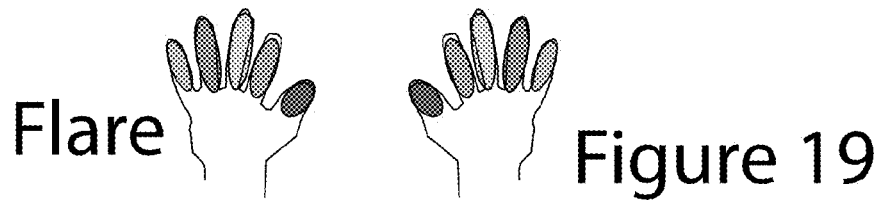
Flare — Figure 19
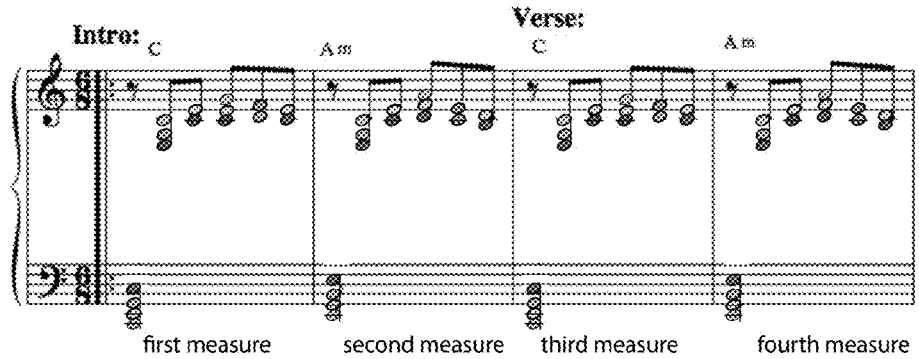
Figure 20
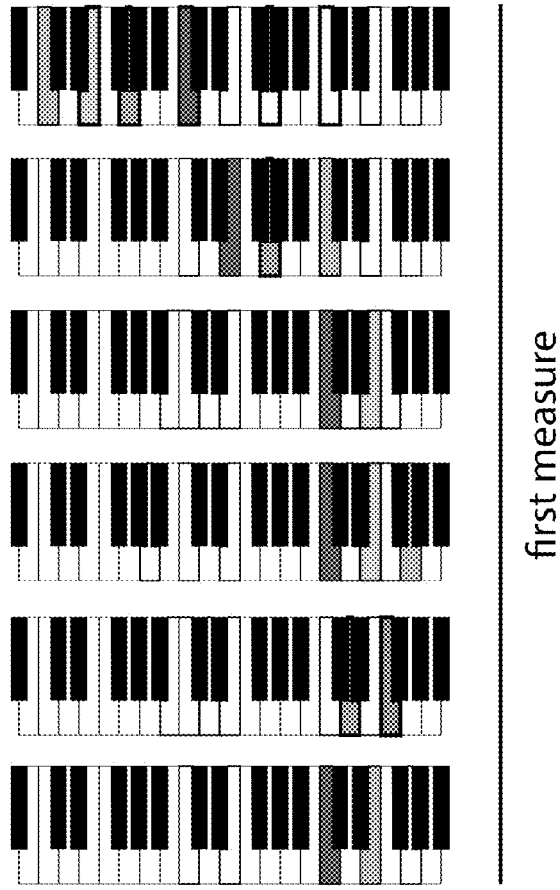
Figure 21

ACCELERATED LEARNING, ENTERTAINMENT AND COGNITIVE THERAPY USING AUGMENTED REALITY COMPRISING COMBINED HAPTIC, AUDITORY, AND VISUAL STIMULATION

CROSS REFERENCE TO RELATED APPLICATION

This Patent Application claims the priority of U.S. Provisional Patent Application No. 61/818,971, filed May 3, 2013, which is incorporated by reference herein in its entirety.

BACKGROUND

The present invention relates to a method and apparatus for providing accelerated learning, entertainment and/or cognitive or physical therapy using augmented and/or virtual reality, comprising combined sensory cues, including, but not limited to, haptic, auditory and visual stimulation.

Augmented reality is a live, direct or indirect, view of a physical, real-world environment whose elements are augmented by computer-generated sensory input such as sound, video, graphics or GPS data. It is related to a more general concept called mediated reality, in which a view of reality is modified (possibly even diminished rather than augmented) by a computer. As a result, the technology functions by enhancing one's current perception of reality. By contrast, virtual reality replaces the real world with a simulated one. (http:/en.wikipedia.org/wiki/Augmented_reality).

Electroencephalography (EEG) is the recording of electrical activity along the scalp. EEG measures voltage fluctuations resulting from ionic current flows within the neurons of the brain. Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are time-locked to more complex processing of stimuli; this technique is used in cognitive science, cognitive psychology, and psychophysiological research. (http://en.wikipedia.org/wiki/Electroencephalography).

An evoked potential or evoked response is an electrical potential recorded from the nervous system following presentation of a stimulus, as distinct from spontaneous potentials as detected by electroencephalography (EEG), electromyography (EMG), or other electrophysiological recording method. Signals can be recorded from cerebral cortex, brain stem, spinal cord and peripheral nerves. Sensory evoked potentials (SEP) are recorded from the central nervous system following stimulation of sense organs (for example, visual evoked potentials elicited by a flashing light or changing pattern on a monitor; auditory evoked potentials by a click or tone stimulus presented through earphones) or by haptic or somatosensory evoked potential (SSEP) elicited by haptic or electrical stimulation of a sensory or mixed nerve in the periphery. There are three kinds of evoked potentials in widespread clinical use: auditory evoked potentials, usually recorded from the scalp but originating at brainstem level; visual evoked potentials, and somatosensory evoked potentials, which are elicited by electrical stimulation of peripheral nerve. See below. (http://en.wikipedia.org/wiki/Evoked_potential).

An event-related potential (ERP) is the measured brain response that is the direct result of a specific sensory, cognitive, or motor event. More formally, it is any stereotyped electrophysiological response to a stimulus. The study of the brain in this way provides a noninvasive means of evaluating brain functioning in patients with cognitive diseases. (http://en.wikipedia.org/wiki/Event-related_potentials).

Fingers do not contain muscles. The muscles that move the finger joints are in the palm and forearm. Muscles of the fingers can be subdivided into extrinsic and intrinsic muscles. The extrinsic muscles are the long flexors and extensors. The fingers have two long flexors, located on the underside of the forearm. The flexors allow for the actual bending of the fingers. The thumb has one long flexor and a short flexor in the thenar muscle group. The human thumb also has other muscles in the thenar group (opponents and abductor brevis muscle), moving the thumb in opposition, making grasping possible. The extensors are located on the back of the forearm and are connected in a more complex way than the flexors to the dorsum of the fingers. http://en.wikipedia.org/wiki/Finger A wireless glove has been developed that can teach piano lessons could help people with spinal cord injuries regain some motor control, according to researchers at Georgia Tech. The fingerless gloves buzz to indicate which piano keys to play, and people who used it in a study experienced improved sensation in their finger. The glove connects to a computer or MP3 player, which is programmed with a specific song or piano piece. This is also connected to a piano with light-up keys. As the keys are illuminated, the glove sends a vibration to the corresponding finger, indicating where and when to tap. This way, the user learns the proper keystroke patterns and memorizes the song. The goal isn't necessarily to learn how to play "Flight of the Bumblebee"—it's so patients with spinal cord injuries can improve feeling or movement in their hands, (http://www.popsci.com/technology/article/2012-07/new-musical-glove-buzzes-your-fingers-haptic-piano-lessons).

This prior attempt is limited to only teaching piano and provides a relatively rudimentary structure that enables a user to learn a simple keystroke pattern and help to memorize a song using haptic stimulation. However, it fails to provide sufficient immersion of the user to enable effective accelerated learning and cognitive therapy using deep immersion augmented and/or virtual reality comprising combined haptic, auditory and visual stimulation. Further, there is no mechanism for effectively capturing the actions of a performer, for example, the stylistic nuances of a performer of a piece of music so that these nuances can be utilized to provide synchronized sensory cues to the student learning to play the piece of music.

SUMMARY OF THE INVENTION

It is an object of the present invention to overcome the drawbacks of the prior attempt and to provide sufficient immersion of a user to enable effective accelerated learning and cognitive therapy using deep immersion augmented reality comprising combined haptic, auditory and visual stimulation.

Many of the embodiments described herein use a musical keyboard as an example of something used to teach a specific technique to a student. In the example of the keyboard, the technique is the playing of a keyboard musical instrument. However, the inventive accelerated learning system is adaptable for use in teaching other musical instruments and is applicable to a wide range of techniques and applications, including, but not limited to entertainment, sporting, military, gaming, and remote control drone or robot operation.

In accordance with an exemplary embodiment for learning a musical instrument, auditory sensory cues capable of being heard a user are generated. The auditory sensory cues comprise a plurality of musical tones played in series and making up a piece of music to be played on keys of a musical instrument. The musical tones comprise one or more individual notes. Each individual note corresponds to a respective key of the musical instrument. In addition to the auditory sensory cues, at least one of haptic sensory cues and visual sensory cues are also generated. The haptic sensory cues are capable of being felt by the user. The haptic sensory cues provide a haptic indication to one or more fingers of the users to indicate which finger is to be used to play each respective key corresponding to the one or more individual notes of the musical tones played on the instrument. The haptic sensory cues are synchronized with the auditory sensory cues so that a predetermined finger that is to play the respective key is stimulated with a haptic sensory cue in synchronization with an auditory sensory cue comprised of the individual note. The visual sensory cues are capable of being displayed to the user. The visual sensory cues provide a visual indication to the user of which finger is to be used to play each respective key corresponding to the individual notes of the musical tone played on the instrument. The visual sensory cues are synchronized with the auditory sensory cues so that the predetermined finger that is to play the respective key is visually indicated in synchronization with the auditory sensory cue comprising the individual note.

The haptic sensory cue can be a vibration applied to the predetermined finger. The vibration can have an intensity corresponding to an audio volume of the individual note. The haptic sensory cue can be an electrical impulse applied to a nerve or muscle corresponding to the predetermined finger. The visual indication can be displayed on a display comprising at least one of a pair of reality augmentation eyeglasses, a computer monitor, a television, a smart phone display or a personal information device display. The visual indication may comprise at least one of a color image, light intensity or light position displayed on a display. The visual indication may comprise at least one of an image displayed on a display of at least one hand indicating the predetermined finger. The visual indication may comprise a light located in proximity to the predetermined finger. The visual information may comprise an image displayed on a display viewed by the user.

In accordance with another aspect of the invention, a mechanism is provided for determining the position of a body member relative to a performance element of a performance object on which an event can be or is to be performed. A conductive glove, keyboard keys with conductive surfaces, and a detection circuit structure are an example of a mechanism for determining the position of a body member relative to a performance element of a performance object on which an event is to be performed. Other examples include a camera and pattern recognition software, or transducers, light detectors, proximity sensors, and the like. The mechanism includes a body member position detector that detects a position of a body member of a performer relative to a performance element of a performance object with which an event is to be performed. For example, the body member position detector can be the conductive glove and the conductive elements on the keys of a keyboard as described by way of example herein. Alternatively, a video camera and computer running pattern recognition software can be used to detect the position of the body member relative to a performance element of a performance object with which an event is to be performed (e.g., fingers relative to the keys of a keyboard on which music is being played). A signal generator generates a signal dependent on the detected position of the body member (e.g., processor and continuity detector). A signal recorder records the signal so that at least one sensory cue can be determined to indicate the position of the body member relative to the element of the performance object during a learning session (e.g., processor and memory storage).

BRIEF DESCRIPTION OF THE DRAWINGS

FIG. 8 schematically shows a potential color coding of the fingers or digits of a user in accordance with the inventive accelerated learning system;

FIG. 9 shows four measures of a piece of music that has a simple single key of the keyboard being pressed at a time in sequence;

FIG. 10 illustrates how each of the four measures of the piece of music shown in FIG. 9 are to be played, with an indication of the keys to be played by the user corresponding to the color coding on the user's fingertips;

FIG. 19 is shown for reference and schematically shows a potential color coding of the fingers or digits of a user in accordance with the invented accelerated learning system;

FIG. 20 shows four measures of a piece of music that is progressively more difficult than the four measures shown in FIGS. 9, 13 and 17, and includes the musical piece played with stylistic flare where multiple keys are to be played simultaneously by both the user's left hand and right hand;

FIG. 21 is an enlarged view illustrating the first measure of the piece of music shown in FIG. 20;

DETAILED DESCRIPTION OF THE INVENTION

Figure 1:
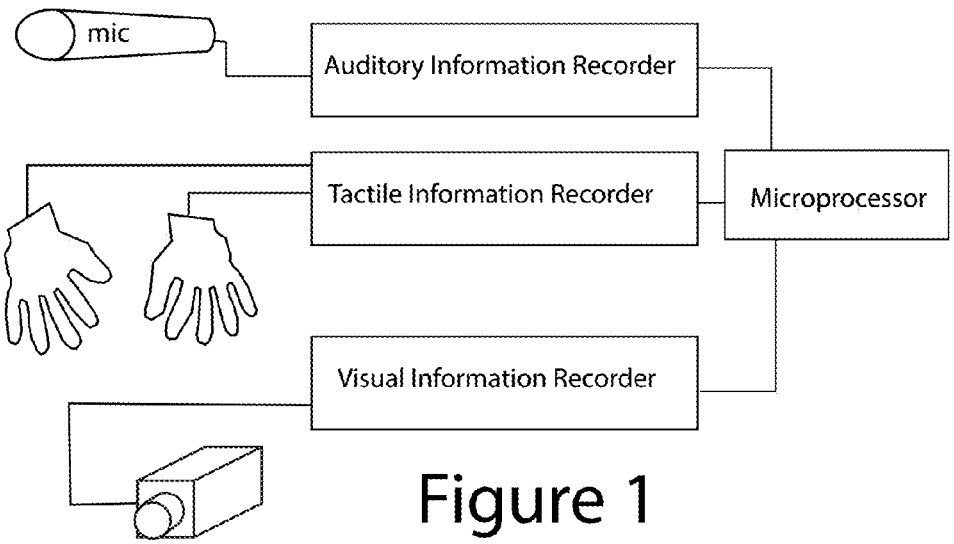
FIG. 1 schematically shows a system for recording haptic, auditory and visual information in accordance with the inventive accelerated learning system.

In accordance with the inventive accelerated learning system, augmented reality is provided through the use of sensory cues, such as audio, visual and touch cues. These sensory cues pertain to an event or action to be learned. For example, the event or action can be the playing of a piece of music at a musical instrument, such as the piano. The inventive accelerated learning system is applicable for other instruments, such as guitar, trumpet, clarinet, woodwind, brass and other musical instruments that employ the selective movement of keys or valves, or the selective fretting of strings on a fingerboard, for example, in conjunction with a serial pattern, such as the playing of a musical piece. The serial pattern may comprise the playing, for example, of notes on a piano by pressing appropriate keys with the fingers. In the case of the piano, the piano keys are played in a serial pattern pertaining to a piece of music. For example, the serial pattern can include cords and other simultaneously or singularly played keys making up a certain tone. The pattern of the keys that are played are detected along with the position of the individual fingers playing the keys. In accordance with the inventive accelerated learning system, this pattern of the fingers relative to the keys being played is recorded, along with various other sensory cues, such as the audio notes of the piano strings being struck when the piano keys are played, the visual perspective of the performer playing the piano, and the haptic sensation of the piano keys being struck by the fingers. A combination of sensory cues, which can include various points of view or perspectives, for example, of the visual position, are used to indicate to the student what the piano key/hand placement pattern is as the piece is learned. In accordance with the inventive accelerated learning system, the learning can occur either remotely or at the instrument. That is, the combination of haptic, audio and visual cues can be The point of view of the user can be as if sitting at the piano looking at the keyboard, the sheet of music, or other generated visual cue perspective. For example, to reinforce the learning of the piece of music with association at various parts of the brain, a colored pattern of the musical notes corresponding to the fingers playing the keys can be generated. Plus, the student receives other simultaneous sensory cues, related to audio, visual and touch. These simultaneously received cues can be given to the student either at the piano, just prior or during the playing of the piece of music, or remotely.

In accordance with an embodiment of the inventive accelerated learning system, the haptic sensory cues can be utilized along with the visual and/or audio sensory cues to create a new kind of entertainment, whereby, a song or visual piece, such as a painting or movie, can be utilized to create the pattern of sensory cues similar to the way described above with reference to learning a musical instrument. However, for example, in this case, instead of learning to play music, the wearer of the inventive haptic gloves, for example can be provided with haptic and visual cues that correspond to the music being played. For example, the sensory cues described above can be recorded or otherwise generated (e.g., by a computer processor, MIDI, or other electronic means). The sensory cues of a piano virtuoso performance can be recorded during the performance and the sensory cues can be used to provide stimulation when the performance is experienced by a listener so that the listening of a musical piece is more enjoyed and/or more deeply experienced.

In accordance with other embodiments of the inventive accelerated learning system, the haptic sensations can be applied to other parts of the body, such as the legs, thighs, arms, ribs, torso, neck, head, etc.

For example, a drumbeat from a musical piece being listened to can be applied as haptic sensations to the legs of the wearer, while the piano performance (such as that recorded as the teaching cues of the piano performer) can be applied as haptic sensations to the fingertips of the use, while simultaneously displaying a visual scene with elements (colors, intensity) synchronized to the musical performance.

In accordance with an embodiment of the inventive accelerated learning system, the sensory cues can be utilized to provide rehabilitation to a victim of a brain injury or other brain damage or learning disfunction. In this case, the various portions of the brain related to the processing of sound, touch and vision can be controllably and simultaneously stimulated so that a weakened brain sensory stimulation processing center can be strengthen or rewired through the support of stronger brain sensory stimulation processing centers. For example, a stroke victim with damage to right side of the brain may have a loss of function in the motor control of the fingers of the left hand. In this case, the haptic sensory cues applied to the fingers of the left hand provide touch sensory stimulation to the damaged portions of the brain, while the corresponding visual and audio cues reinforce the re-learning or rewiring of the damaged portions of the brain through the touch sensory stimulation.

FIG. 1 schematically shows a system for recording haptic, auditory and visual information in accordance with the inventive accelerated learning system. To record the audio, haptic and visual information during, for example, a piano session, finger position sensing gloves can be used with a digit/key detecting keyboard. They microphone is used to record the notes played on the piano. The user wears conductive gloves so that the piano keys that are played, can be determined, as will be further described below. The microphone simultaneously records the sounds generated by the piano when the piano keys are played. Further, a visual information recorder, such as a video camera or specially constructed eyeglasses that include a camera, are used to record from the performers perspective, the hand and finger positions of the performer while playing the piano. By this system, the experience of the piano player is recorded from the perspective of three sensing cues: audio, visual, and haptic.

Figure 2:
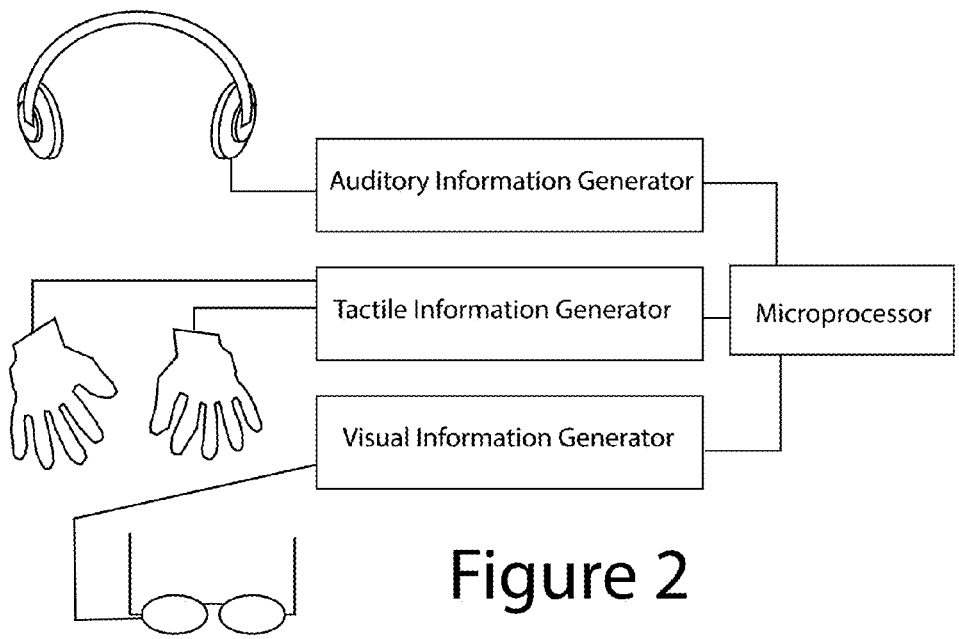
FIG. 2 schematically shows a system for playing back recorded audio, visual and haptic information during an accelerated learning session.

FIG. 2 schematically shows a system for playing back recorded audio, visual and haptic information during an accelerated learning session. In accordance with the present invention, accelerated learning is achieved by simultaneously stimulating the auditory, visual and haptic senses of a user, to simulate and augment an actual performance of an event, such as the playing of a song on a musical instrument, for example, a piano. Recorded or artificially generated sensory cues are provided to the user through an auditory information generator, haptic information generator and visual information generator. The respective generators are connected to and activate a corresponding interface device, such as headphones, gloves and displays. For example, in the case of a haptic information generator, a vibration buzzer (such as a piezo or motor driven mechanical vibrator) can be applied to the individual fingers of the user, for example, the student during a lesson learning session. In the case of the display, it may be, for example, specially constructed eyeglasses that display visual information that has been recorded or artificially created corresponding to the learned event. Specially constructed eyeglasses may display generated visual information as an overlay, picture in a picture, or other simultaneously displayed video information while the user also sees the real world imagery. For example, when learning to play the piano, the student may be sitting at the piano and able to see a sheet of music and also see the piano keys with his hand and finger positions in real time, while also seeing visual sensory cues that is being generated and supplied to the specially constructed eyeglasses. Also, the accelerated learning may take place remote from the instrument, so that the user feels, hears and sees sensory cues corresponding to the learning of the event at any time and place remote from the instrument. This accelerated learning system is designed to create associative memory in the user corresponding to muscle memory (haptic information), auditory memory (auditory information), and visual memory (visually display information). The inventive accelerated learning system obtains the memory associations of the sensory cue whether at the piano or remote from the instrument. Plus, the user is more able to reinforce the associate to memories of the sensory cues that make up the performance of an event, such as the playing of a piece of music.

Figure 5:
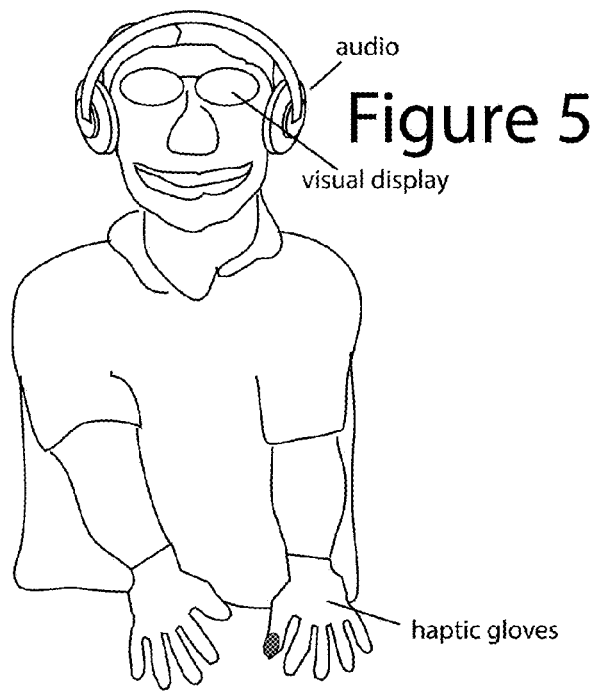
FIG. 5 shows a hand of a student wearing haptic/visual gloves and headphones that indicate to the student the haptic, visual and audio cues corresponding to the learning session.

FIG. 2 schematically shows a system for playing back recorded audio, visual and haptic sensory cues during an accelerated learning session. FIG. 5 shows a hand of a student wearing haptic/visual gloves and headphones that indicate to the student via vibrators, for example, the haptic cues corresponding to the learning session. To record from the performers visual perspective, video recording glasses such as Google glass, can be used. Visual and audio playback when in lesson mode can be done using video glasses that include headphones. Haptic gloves are worn that include a buzzer or vibrator on each finger and can also include an LED on each finger or located near each finger tip. For example, the student will receive the same visual cues as received during a remote learning session to create a learned visual memory of what the student will visually experience when seated at the piano.

Figure 3:
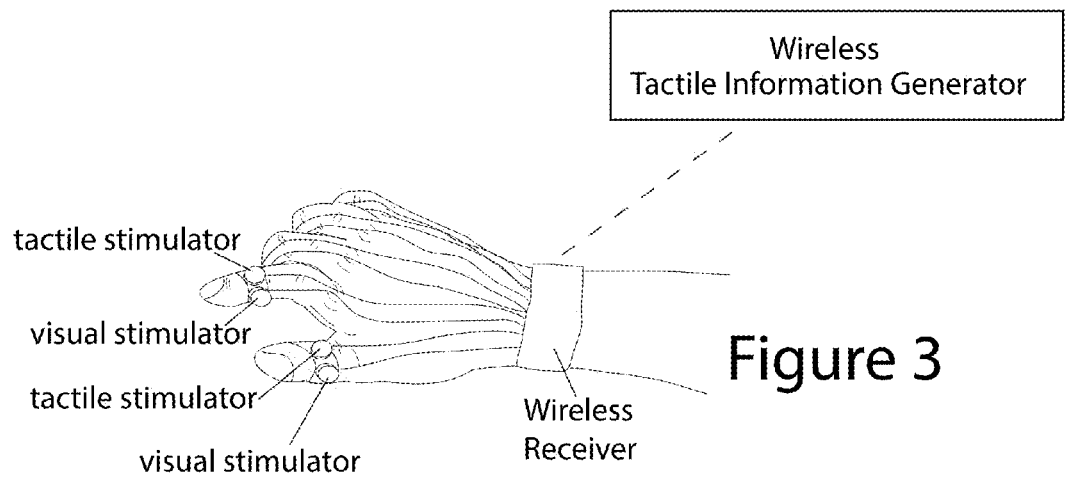
FIG. 3 shows an embodiment of a wireless haptic information and visual information generator/recorder.

FIG. 3 shows an embodiment of the haptic sensory cue and visual sensory cue system. In this case, the user has haptic stimulators and visual stimulators associated with each finger on their hands. When, for example, learning to play the piano, the haptic stimulator and the visual stimulator associated with each finger correspond to the finger that was used by the performer when the event was recorded.

Figure 4:
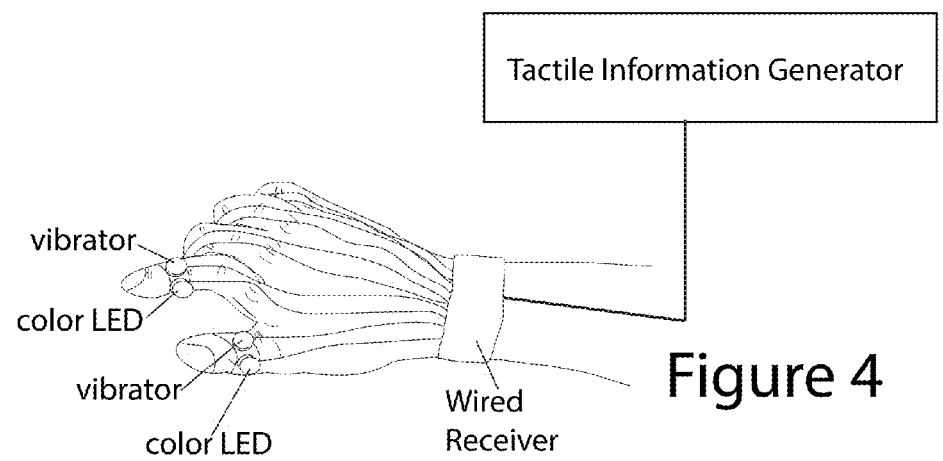
FIG. 4 shows an embodiment of a wired haptic information and visual information generator/recorder.

FIG. 4 shows an embodiment of the inventive haptic and visual sensory cue generator. In accordance with this embodiment, the user (the student) wears haptic stimulators and visual stimulators on the tips of their fingers. The haptic stimulators can be, for example, small buzzers, the haptic stimulator can be a mechanism that applies an electrical pulse directly or indirectly to the muscle or muscle groups of the user to cause a sensation or contraction in that muscle group that corresponds to a particular finger that is to be used to play, for example, a key on the piano during the learning session. It is noted that the learning session may be performed while seated at the instrument, and can also take place remote from the instrument. For example, the memories associated with the playing of a piece of music, in accordance with an embodiment of the invention, will include audio, visual, and tactile (haptic or other stimulation) cues that are generated and that can be repeated over and over to instill the associative memory that is built up during the course of conventional music practice at an instrument.

FIG. 3 and FIG. 4 show embodiments of haptic sensory cue and visual sensory cue generator/recorder. A colored light emitting diode (LED), color paint, or other indication can be provided on the finger or fingertip of the performer, and the hand positions can be recorded as video sensory cue while playing the piece. When a piano key is played, the key being played and finger playing the key are recorded. During an in-situ (at the instrument) or remote (remote from the instrument) learning session, the student receives multiple simultaneous sensory cues that pertain to the recorded lesson. For example, in accordance with an embodiment of the invention, the student hears the note(s), feels a buzz on the finger(s) and sees the hand pattern. The visual sensory cue can be recorded from the performer's perspective including a visual indication of which finger is playing a key. This can be done at anytime, it is not necessary for the student to be sitting at the piano. The multiple simultaneous sensory cues create a lesson memory that includes muscle memory (haptic), audio memory and visual memory. This students learned lesson memory is reinforced by repeated sessions.

FIG. 5 shows a hand of a student wearing haptic/visual gloves and headphones that indicate to the student the haptic, visual and audio cues corresponding to the learning session. A user (performer and/or student) wears haptic/visual gloves that indicate to the user the haptic and visual cues corresponding to the learning session, for example, the playing of a piece of music during the recording and learning of the learning session. The user may also wear headphones to hear the audio cues (or, the audio cues may be presented from speakers or other auditory stimulating mechanism). The user may further wear a pair of visual/audio recording/display glasses, such as, for example, Google glass.

Thus, as will be described in more detail below, the user receives different audio, visual, and haptic cues to indicate the notes or keys being played, for example, on a piano during a learned piece of music. For example, the user may receive visual cues through the lighting up of LED lights on the fingertips of the users that correspond to the fingers playing a key on a piano. Simultaneously, or alternatively, the nerves of the skin and muscles corresponding to the finger may be stimulated via vibrations or electrical impulses so that muscle memory of the learned piece of music is built up in conjunction with the auditory and visual cues.

Figure 26:
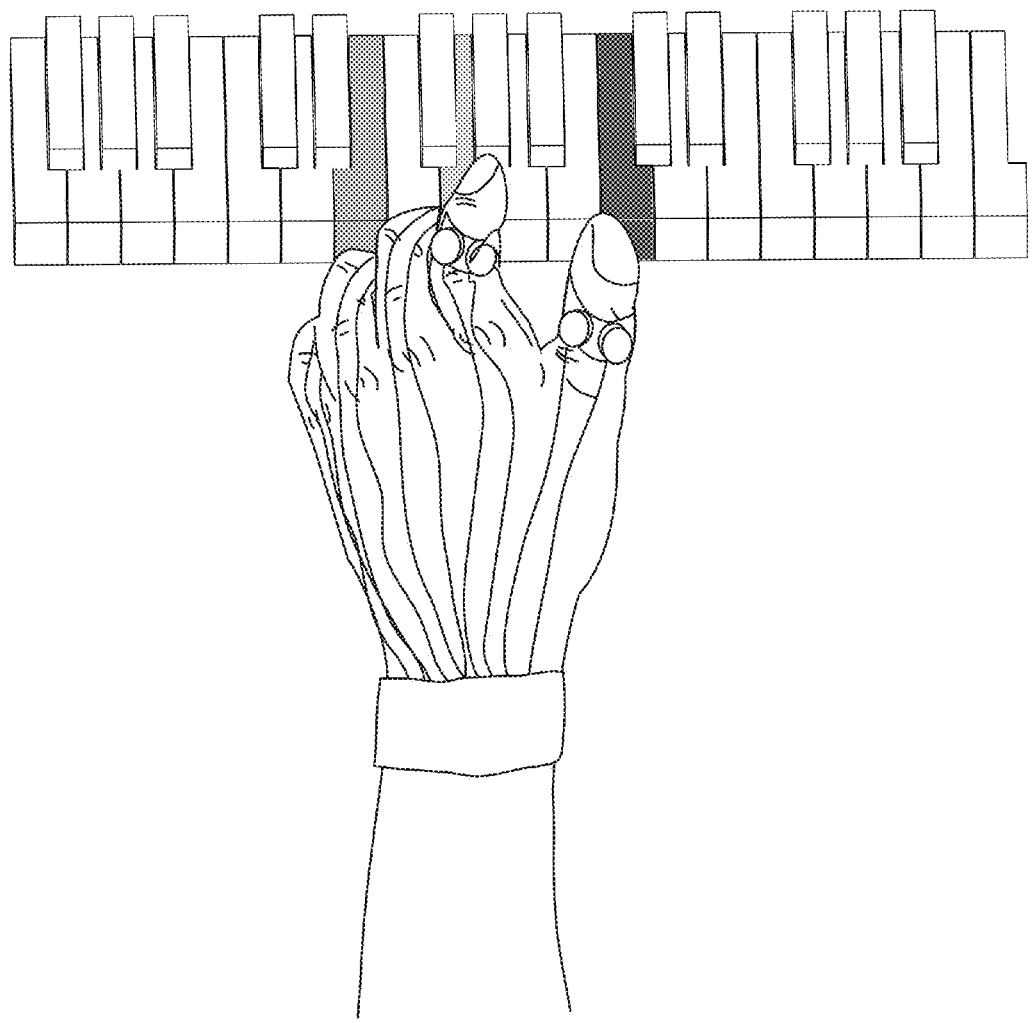
FIG. 26 illustrates yet another visual perspective of the keyboard that can be displayed to the student as a visual sensory cue.

Using the inventive accelerated learning system, a student receives simultaneous sensory cues, which may be similar to the sensory cues that are received during an actual practice session at an instrument, or that may be different than an actual practice session experience. As an example of an actual practice session experience, a visual sensory cue may be a display showing the keyboard with the hand positions from the perspective of the performer. FIG. 26 illustrates for example a visual perspective of the keyboard that can be displayed to the student as a visual sensory cue, in this case the visual perspective corresponds to the viewpoint of the performer. In this case, the recording of the visual cues can be done using a head-mounted video camera, or a pair of augmented reality glasses that include a video camera. As an example of a sensory cue that is different than an actual practice session experience, a visual sensory cue can be artificially generated that corresponds to the learning session. In this case, for example, images such as the sequence of images shown in FIG. 11 can be display to the student in synchronization with the audio sensory cues and/or the haptic sensory cues applied during the learning session. Further, different versions of the same type of sensory cues can be applied simultaneously. In this case, as an example, the viewpoint of the performer shown in FIG. 26 can be displayed in the center of the student's field of view while at the same time the generated sequence of images shown in FIG. 11 can be displayed in a peripheral portion of the student's field of view. Simultaneously, the corresponding audio sensory cues and haptic sensory cues can be provided to the student. Further, the audio sensory cues and the haptic sensory cues may also be varied to achieve a specific goal. For example, the audio sensory cues corresponding to the haptic sensory cues applied to right hand may be applied to the left ear of the student, or vice-versa, depending on the portions of the brain that are desired to be simultaneously stimulated. These generated sensory cues will be received by different parts of the users brain, to create an associated processing and memories between the various parts of the brain that are stimulated. The student, or person being rehabilitated, or person being entertained, experiences, for example, the piece of music with the reinforcement of the associated memories resulting from the simultaneously applied sensory cues. This experience can occur during practice sessions at an instrument and/or remotely from the instrument.

In accordance with an embodiment of the inventive accelerated learning system, to further enhance the learning experience, chemicals released by the brain systems can be detected from a student that is actually learning the piece of music at a practice session at the instrument. As another example, the brain activity of a student can be sensed using well-known brain scan techniques (such as those described in the background) and the applied sensory cues can be the focus of the different brain activities related to auditory, visual, and haptic sensory cue processing to further reinforce and enhance the learning experience. The inventive accelerated learning system can be applied to other activities, including but not limited to sports, school work, performing arts, military exercises, video gaming, etc.

An embodiment described herein pertains to learning to play music on a keyboard. However, the inventive accelerated learning system is not at all limited to keyboards, or to learning to play music. As is also described herein, aspects of the inventive accelerated learning system can be utilized for a number of different fields, including entertainment, military, sports, video gaming, remote controlled robots, drones and vehicles, other musical instruments, etc.

Figure 6:
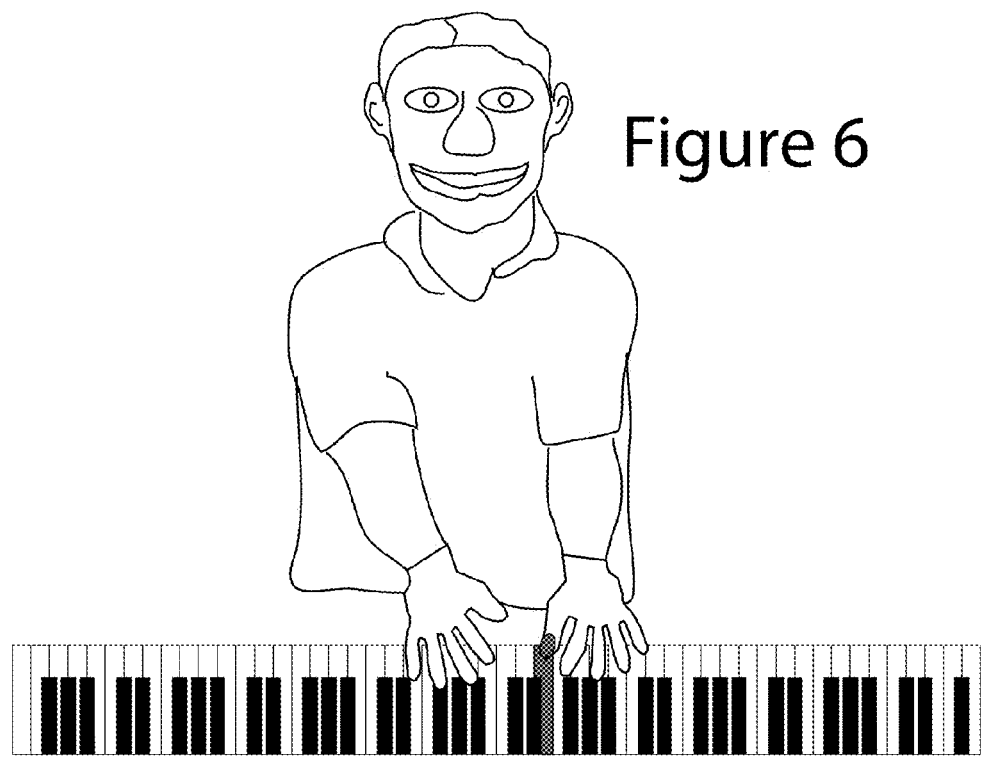
FIG. 6 shows a user sitting at a digit/key detecting keyboard wearing a haptic information and visual information recorder gloves, and audio and video information recorder glasses having a head-mounted video camera and a microphone, during the recording of a music lesson to be used in accordance with the inventive accelerated learning system.

FIG. 6 shows a user sitting at a keyboard, during the recording of a music lesson to be used in accordance with the inventive accelerated learning system. In this case, as will be described more fully below, the keyboard is specially constructed so that each key being played sequentially or in combination with other keys during the piece of music is determined, along with which finger or fingers of the users hand corresponds with which keys of the instrument being depressed. Thus, not only are the keys recorded (as can be done using, for example, a MIDI keyboard), but also the pattern of the actual fingers used during the playing of a musical piece are determined and recorded. This is an important consideration, especially when learning a keyboard instrument, because the particular pattern of the fingers used to play, for example, a cord, should be imparted to the student during the learning session in order to properly set up for the sequential playing of keys on the keyboard when playing the piece of music. For example, a C chord can be played, comprising the notes corresponding to the C key, the E key, and the G key. The finger pattern use to the depress the keys during the playing of a piece of music greatly depend on the keys depressed sequentially before and sequentially after the cord is played. Thus, which fingers of the performer are used to depress which keys during the recording of the learning session are determined in accordance with the inventive accelerated learning system. The student is then able to receive the proper haptic sensory cue so that the sequence of the keys that are depressed when playing the piece of music can be properly learned and played.

Figure 7:
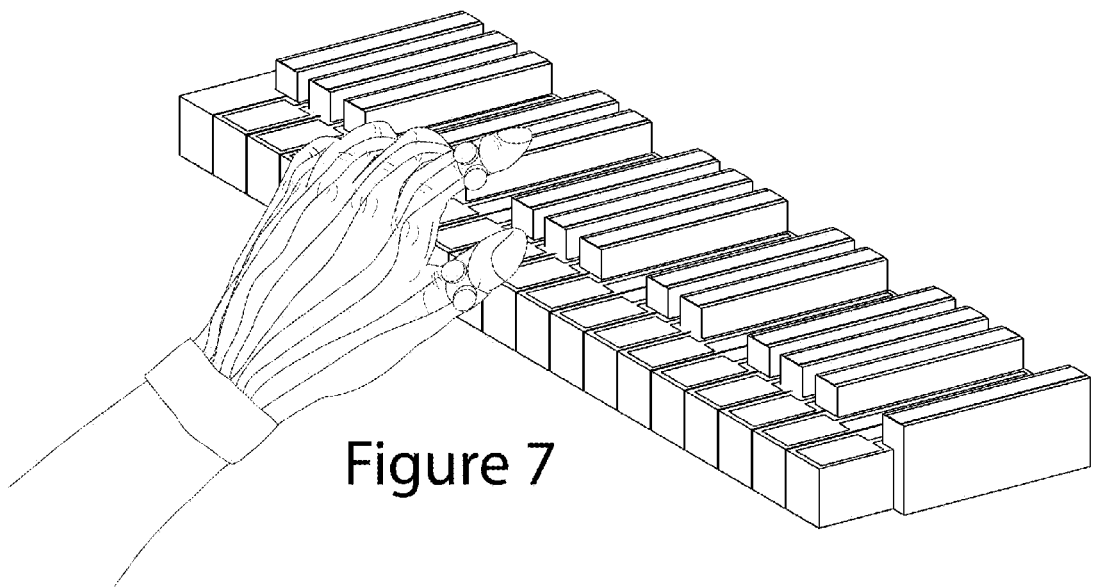
FIG. 7 is an isolated view of a specially constructed digit/key detecting keyboard and a user's hand wearing haptic information and visual information recorder in accordance with the inventive accelerated learning system.

FIG. 7 is an isolated view of a specially constructed digit/key detecting keyboard and a user's hand (performer or student) wearing haptic sensory cue and visual sensory cue recorder/player in accordance with the inventive accelerated learning system. The specially constructed keyboard includes a sensing mechanism that is used to determine not only which key is being activated, but which finger is activating the key. Also, false readings of the key and fingers circuit (for example, when a finger rest upon a key but is not depressing it) can be subtracted from the recorded sensory cue by determining which key or keys are actually contributing to the intended cord or tone being generated by the instrument. In this case, for example, well known MIDI devices and techniques can be used to determine which keys are actually contributing to the intended tone. Alternatively, sound processing of the received sound frequencies can be employed to determine which keys are actually contributing to the intended tone. This sound processing can make the digit/key detecting keyboard a practical retrofit, for example, to an existing acoustic piano.

Figure 11:
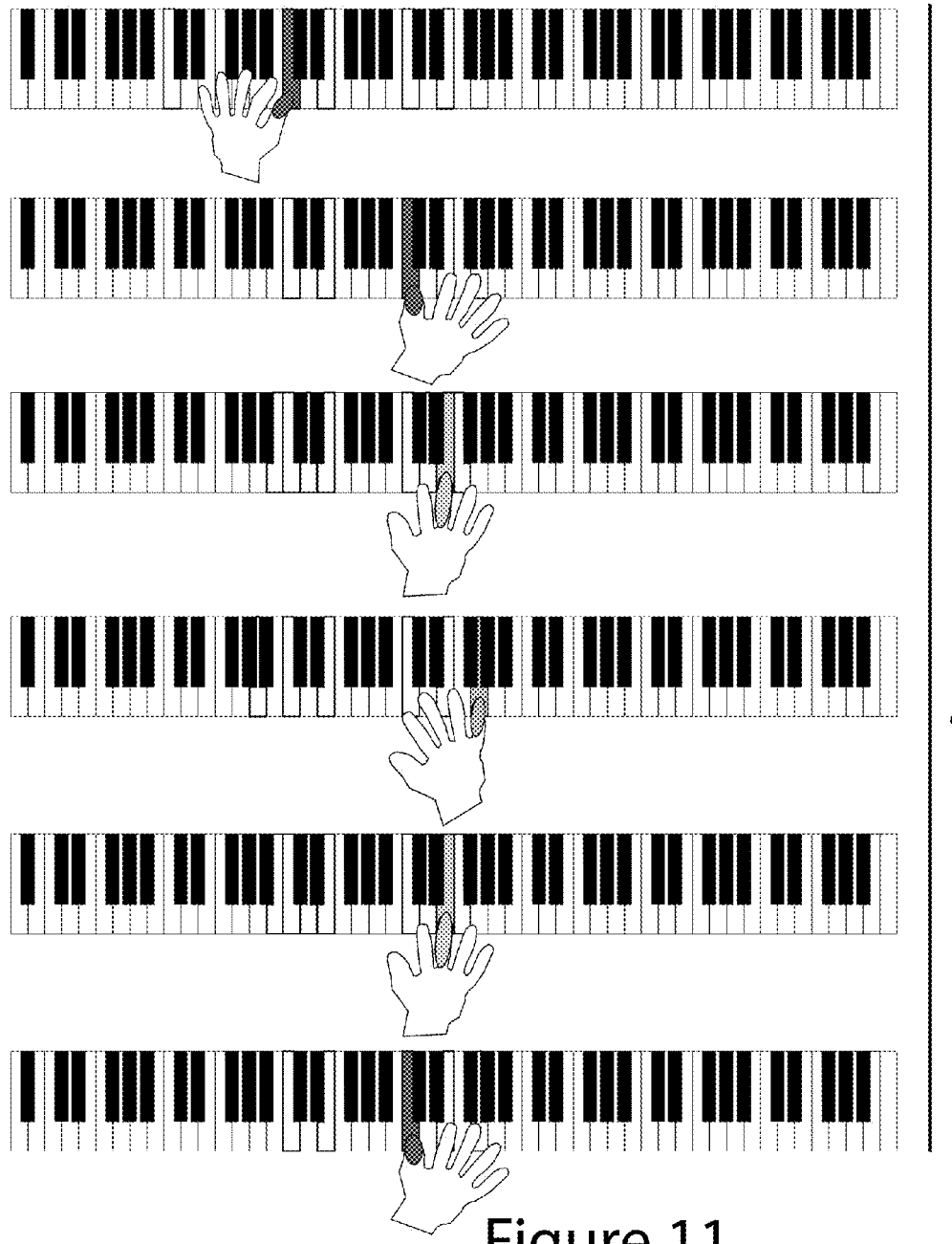
FIG. 11 is an enlarged view illustrating the first measure of the piece of music shown in FIG. 10.

FIG. 8 schematically shows a potential color coding of the fingers or digits of a user in accordance with the invented accelerated learning system. FIG. 9 shows four measures of a piece of music that has a simple single key of the keyboard being pressed at a time in sequence. FIG. 10 illustrates how each of the four measures of the piece of music shown in FIG. 9 are to be played, with an indication of the keys to be played by the user corresponding to the color coding on the users fingertips. FIG. 11 is an enlarged view illustrating the first measure of the piece of music shown in FIG. 10.

In the example shown, the fingers of one hand has the same color code as the corresponding finger of the other hand. This color coding can correspond to a variety of visual cues, including colored LED lights affixed to the gloves or directly to the fingers of the user, as described in more detail herein. Also, the color coding can be applied to other visual patterns that can be computer generated or otherwise simulated. For example, the finger color coding can be represented on an image of a keyboard displayed to the user (student and/or performer), on the keys of the keyboard itself. For example, the pinkies of the right and left hands of the user may both have the same color code blue. In accordance with the inventive accelerated learning system, the color associated with each finger can be generated using an appropriate colored LED. Alternatively, or in addition, the color coding of the finger can be done using tracking software and artificially created through a computer algorithm and then generated through the visual display system.

The inventive accelerated learning system can employ the use of augmented reality eyeglasses, such as those available from Google glass and Vuzix, smart phones, computer displays or other appropriate display mechanism that can, for example, display a visual sensory cue, such as, but not limited to, overlay a visual cue of a color to each finger during the learning session. In accordance with an embodiment of the inventive accelerated learning system, tracking of the performer's fingers during the recording of the lesson can be done using reflectors, transducers or proximity sensors, on the fingertips of the user. Also, the position of the user's (performer or student) fingers relative to the keys being depressed can also be tracked using pattern recognition software so that the electrical circuitry for example shown in FIG. 27 can be augmented or avoided and any keyboard can then be employed.

As an alternative to reflectors or lights applied to the fingers, the individual fingers themselves can be tracked by determining their location using pattern recognition software. The fingernails of the user can be painted with a suitable colored or reflective paint. If a MIDI system is used, the keys being depressed that generate the tone can be determined by the circuitry and the software of the MIDI system. For a conventional acoustic piano, the tone being played can be broken down into the individual notes by detecting the a sound wave form, and assigning the corresponding key to the appropriate peak. By noting which finger is located in close proximity to which key, the correct finger/key relationship can be determined.

FIG. 8 schematically shows the right and left hands of a student with the color-coded fingertips. The color-coded fingertips may correspond to, for example, colored lighting on the fingertips, reflective material applied, for example, to the fingernails, and a reflection detected by detecting circuitry including a photodetector. For example, during the stimulation of the visual sensory cues, in accordance with the inventive accelerated learning system, the overlay image of the colored fingertips can be displayed using, for example, augmented reality glasses, over the actual or displayed images of the fingers of the student. In this case, a computer generated image corresponding to the color-coded fingertips can be shown in conjunction the position of the actual fingers of the student while, for example, playing the keyboard.

FIG. 9 shows four measures of a piece of music that has a relatively simple level of difficulty with a single key being pressed in sequence. That is, there are no cords or portions of cords being played in this most simple example of a learned piece of music. Also, the left hand and the right-hand are not required to simultaneously play a key at the same time. As is described in more detail below, in accordance with the inventive accelerated learning system, the student may advance to more difficult versions of the same piece of music, so that the associated memories in the different processing centers of the brain are also progressively enhanced. The color coded measures of the piece of music can be provided, for example, on a digital display such as a monitor or augmented reality eyeglasses. Also, the notes played by the user can be, determined and matched up with the correct notes displayed as the musical notation. A score can be provided letting the user know how well the piece of music was played, where progress is being made or improvements needs to be focused, and when it is time to advance to the next level of the progressively advanced music lessons.

FIG. 10 shows each of the four measures of the piece of music shown in 9, with an indication of the keys to be played by the user corresponding to the color coding on the users fingertips. FIG. 11 is a larger view showing the keyboard and the fingers of the user striking the key of the keyboard while playing the learned piece of music.

Figure 12:
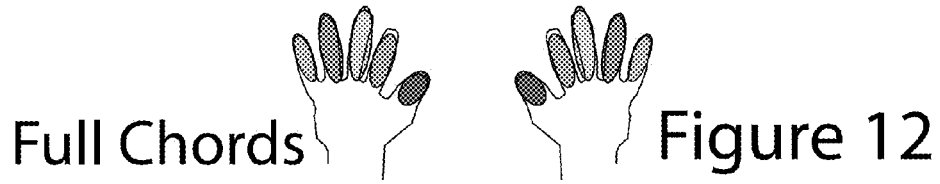
FIG. 12 is shown for reference and schematically shows a potential color coding of the fingers or digits of a user in accordance with the invented accelerated learning system.
Figure 13:
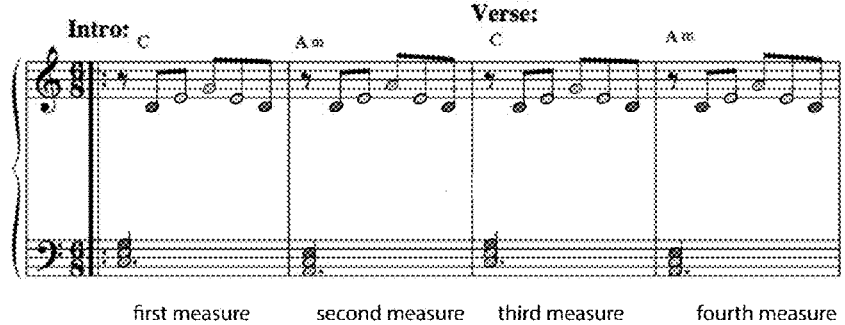
FIG. 13 shows four measures of a piece of music that is progressively more difficult than the four measures shown in FIG. 12, and includes full chords comprising three keys to be played simultaneously by the user's left hand and single keys of the keyboard being pressed at a time in sequence by the fingers of the user's right hand.
Figure 14:
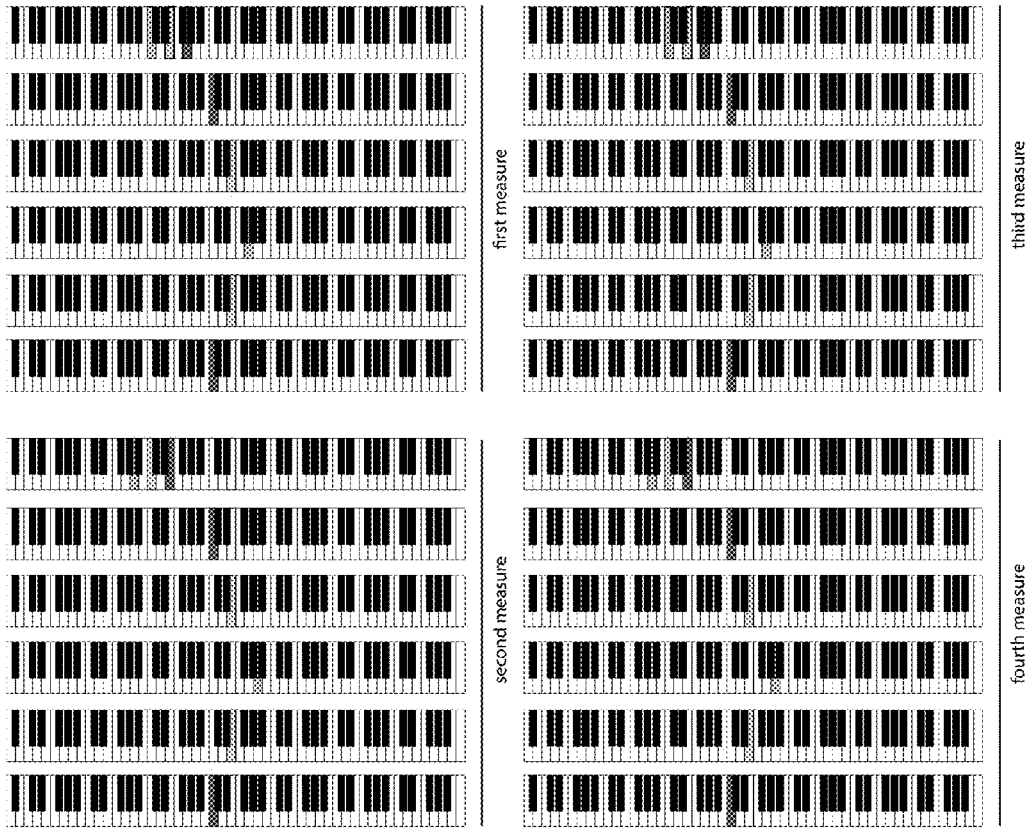
FIG. 14 illustrates how each of the four measures of the piece of music shown in FIG. 13 are to be played, with an indication of the keys to be played by the user corresponding to the color coding on the user's fingertips.
Figure 15:
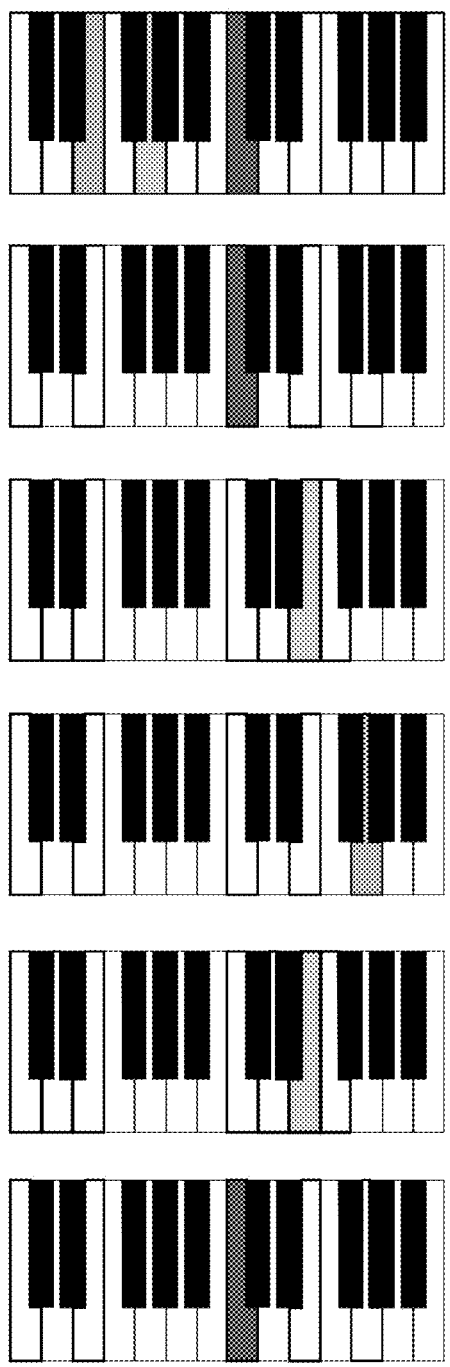
FIG. 15 is an enlarged view illustrating the first measure of the piece of music shown in FIG. 14.
Figure 16:
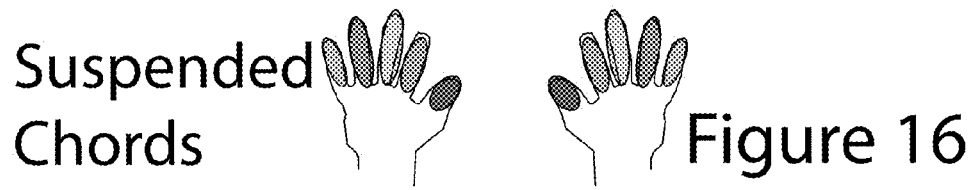
FIG. 16 is shown for reference and schematically shows a potential color coding of the fingers or digits of a user in accordance with the inventive accelerated learning system.
Figure 17:
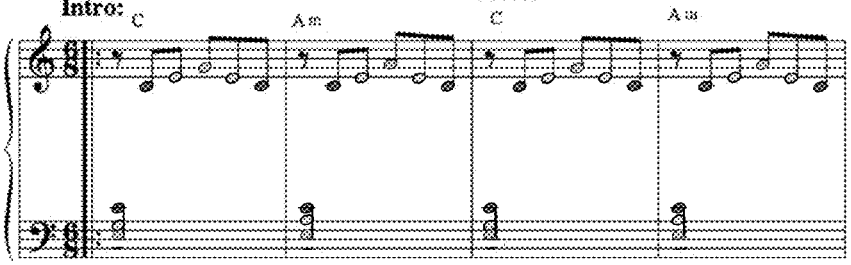
FIG. 17 shows four measures of a piece of music that is progressively more difficult than the four measures shown in FIGS. 9 and 13, and includes suspended chords comprising multiple keys to be played simultaneously by the user's left hand and single keys of the keyboard played in sequence by the fingers of the user's right hand.
Figure 18:
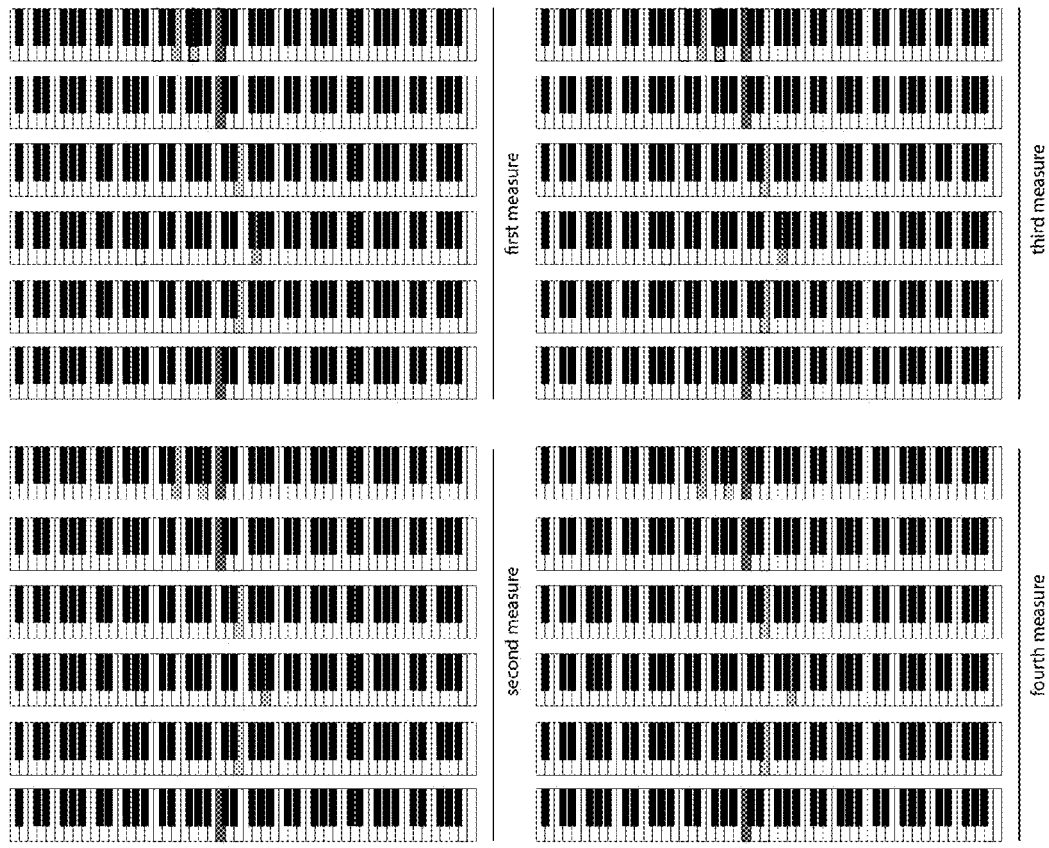
FIG. 18 illustrates how each of the four measures of the piece of music shown in FIG. 17 are to be played, with an indication of the keys to be played by the user corresponding to the color coding on the user's fingertips.

FIG. 12 is shown for reference and schematically shows a potential color coding of the fingers or digits of a user in accordance with the inventive accelerated learning system. FIG. 12 again shows the color-coded fingers of the user. The same color coding of the performer's fingers during the lesson recording session and the student's fingers during the lesson learning session can be used. FIG. 13 shows four measures of a piece of music that is progressively more difficult than the four measures shown in FIG. 12, and includes full chords comprising three keys to be played simultaneously by the user's left hand and single keys of the keyboard being pressed at a time in sequence by the fingers of the user's right hand. FIG. 13 shows the piece of music shown in FIG. 9, this time, the performance has become progressively more difficult. In this case, the left hand of the user plays chords, while the right-hand continues to play a more simplistic melody. Thus, the student is gradually introduced to a progressively more difficult musical performance of the same piece of music. FIG. 14 illustrates how each of the four measures of the piece of music shown in 13 are to be played, with an indication of the keys to be played by the user corresponding to the color coding on the users fingertips. FIG. 15 is an enlarged view illustrating the first measure of the piece of music shown in FIG. 14. FIG. 16 is shown for reference and schematically shows a potential color coding of the fingers or digits of a user in accordance with the inventive accelerated learning system. FIG. 17 shows four measures of a piece of music that is progressively more difficult than the four measures shown in FIGS. 9 and 13, and includes suspended chords comprising multiple keys to be played simultaneously by the user's left hand and single keys of the keyboard being pressed at a time in sequence by the fingers of the user's right hand. FIG. 18 illustrates how each of the four measures of the piece of music shown in 17 are to be played, with an indication of the keys to be played by the user corresponding to the color coding on the users fingertips. FIG. 19 is shown for reference and schematically shows a potential color coding of the fingers or digits of a user in accordance with the invented accelerated learning system. FIG. 20 shows four measures of a piece of music that is progressively more difficult than the four measures shown in FIGS. 9, 13 and 17, and includes the musical piece played with stylistic flare where multiple keys are to be played simultaneously by both the user's left hand and right hand. FIG. 21 illustrates how each of the four measures of the piece of music shown in FIG. 20 are to be played, with an indication of the keys to be played by the user corresponding to the color coding on the users fingertips.

FIGS. 8-21 show the musical performance becoming progressively more difficult and the skills of the student becoming more advanced through the inventive accelerated learning system. In this case, the music that is played by the student has suspended chords which require an advancement in the technique of hand placement and music reading. Thus, it can be appreciated that the inventive accelerated learning system which employees sensory cues that include audio, visual, and haptic sensory cues that cause associative connections of these cues to be made in the different processing centers of the student's brain, whether the student is actually sitting at the instrument or is remote. Further, it is contemplated that the inventive accelerated learning system will be particularly useful during restful states of the student. For example, research into dreaming has shown that there are several stages of sleep. In accordance with the inventive accelerated learning system, the user or student can receive the sensory cues during a particular stage of the sleep process. It is contemplated, for example, that the restful state known as non-REM sleep may be particularly advantageous to this accelerated learning system. In accordance with an aspect of the invention, the sleep state can be detected using well-known sleep state detecting techniques, and the lesson learning session is made to occur during this sleep state. Alternatively, other restful, wake or sleep states can be targeted for the lesson learning session to occur.

FIGS. 19-21 show the progression of the learned piece of music, this time, the learning piece of music includes the stylistic form of the performance of the piece of music. In this case, the flare, or style, of a particular musician can be recorded as the sensory cues that can be then played back to a student learning to play the piece of music and obtain a sense of the style and flair of the particular performer. Through the immersion of the student in to the performance of the performing musician, the student can obtain through associative memory the cognitive and muscle memory to acquire at least some of the stylistic actions and nuances of the performing musician. For example, a performing musician may have the use of trills and other quick keys played in succession which may be difficult for a novice student master. The inventive accelerated learning system builds up the associated memories in the processing centers of the student's brain related to audio, visual and tactile experiences or cues. To teach music reading, the musical notation (sheet music or as a displayed image) can also be provided to the student along with the sensory cues of audio, haptic and visual stimulation remotely, and/or in conjunction with learning the piece of music at the instrument. As with other visual aspects, the sheet music can be located in the real world (that is, for example, on a music stand) while other images (e.g., the performer's hands superimposed on the actual keyboard) or color-coded patterns can be generated and presented in augmented and/or virtual reality using, for example, Google glass. By tracking the position of the student's head and/or eyes, the scene displayed for the augmented reality can be adjusted. For example, when looking down toward the keyboard, the augmented reality can be the color-coding described above superimposed on the student's fingers, when looking at the sheet music on the piano music stand, the augmented reality can be the color-coded pattern. As another alternative, the sheet music can be displayed with the color-coding described herein, or augmented reality can be used to superimpose the color coding on the real world sheet music.

Figure 22:
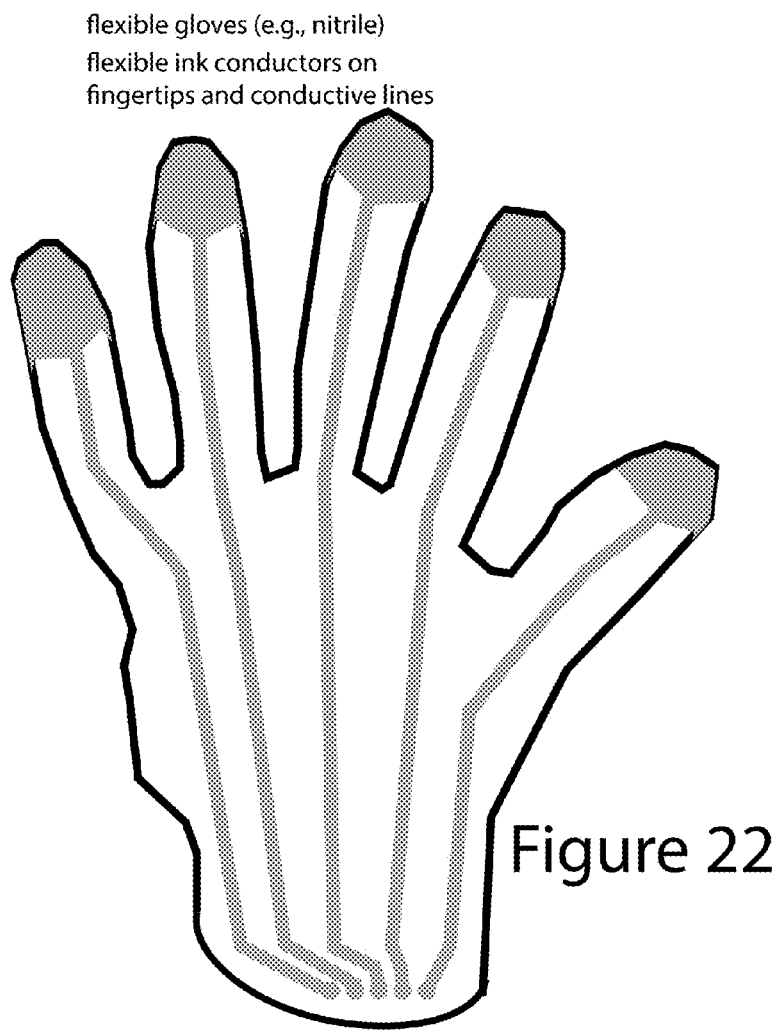
FIG. 22 illustrates a glove having conductive fingertips and conductive lines connected to the conductive fingertips.

FIG. 22 illustrates a glove having conductive fingertips and conductive lines connected to the conductive fingertips. FIG. 22 shows an embodiment of a flexible glove used to obtain the musical haptic cues in conjunction with the electronic circuit keyboard structure described herein. In this case, in a simple form, the Gloves can be constructed using, for example latex or other flexible glove material. The fingertips of the gloves are dipped in a conductive ink, which includes typically conducted particulate such as silver held within a flexible binder. The fingertips of the gloves are thus made to be individually conductive, so that a completed electrical circuit can be sensed when the user depresses a key on the digit/key detecting keyboard described herein. Wiring lines can also be wired, painted, soldered, silkscreened or otherwise disposed on the gloves so that individual connection can be detected when a fingertip of the user completes the electrical circuit when striking a key on the electronic digit/key detecting keyboard. In accordance with an embodiment of the present invention, tight fitting gloves can be used, such as vinyl, latex, rubber, or nitrile gloves, with the finger tips of the gloves dipped in a conductive paint. In the event that two or more keys are struck it once by the same finger only take the keys that have stuck a key of the keyboard with enough force to create a note being played are detected, so that a slight connection between the finger and an unintended key is not recorded as part of the recorded lesson.

Figure 23:
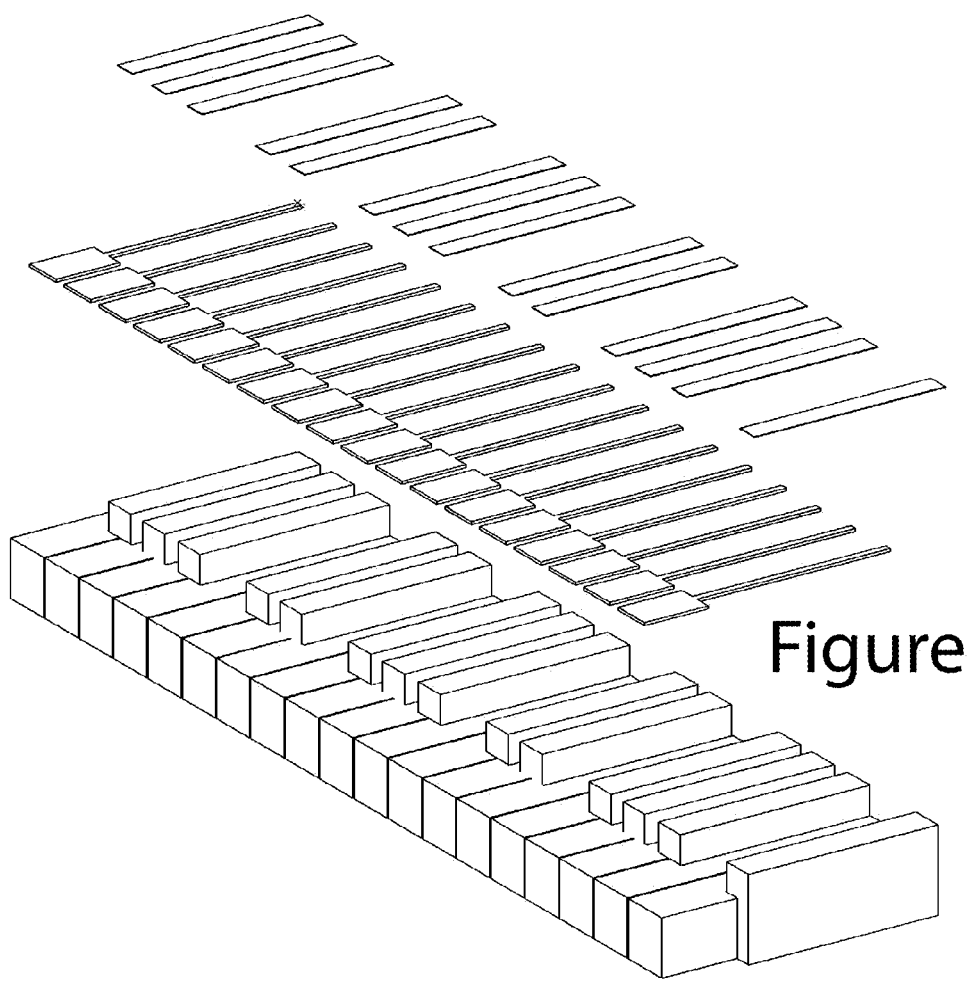
FIG. 23 schematically shows an exploded view of a digit/key detecting keyboard having conductors associated with each key for use with the glove shown in FIG. 22.

FIG. 23 schematically shows an exploded view of a digit/key detecting keyboard having conductors associated with each key and for use with the glove shown in FIG. 22. FIG. 23 shows an exploded view schematically illustrating the conductive surfaces of the inventive digit/key detecting keyboard, and the keys of the keyboard. In this case, the keyboard keys can be specifically constructed, or an existing keyboard (acoustic or electric) can be retrofitted to act as the digit/key detecting keyboard. For example, conductive tape, such as copper tape with adhesive backing, can be used to make the conductive surfaces on the black and white keys of the keyboard. Alternatively, the keyboard can be constructed so that the electronic circuit is completed when the individual finger of the user wearing the conductive gloves strikes a particular key of the electronic circuit keyboard. By this construction, not only is the key of the keyboard detected when a piece of music is performed, but also the particular finger used to strike the key is also detected. By doing so, the position of the fingers and hands of the performer, and the keys being used to strike each key or keys being played to perform the piece of music, are detectable so that they can be recorded to later be used to generate the sensory cues received by a student during a learning session. By knowing which keys are associated with which fingers during the performance of a piece of music, the student can then be given the appropriate haptic visual and audio cues so that the piece of music can be learned either remotely or when sitting at the instrument.

As shown in FIGS. 7 and 23, the specially constructed keyboard includes electrodes disposed on the top faces of the black and white keys of the keyboard. The electrodes can be, for example, metallic strips adhered to a keyboard, or other conductors such as conductive ink or conductive tape applied to the keys. As shown, for example, in FIG. 22, the performer and/or student may wear specially constructed gloves that have digit (i.e., finger or finger tip) conductive pads that are terminated by wires so that an electrical signal can be selectively determined or applied (via, for example, a vibrator, not shown) corresponding to a finger being used to depress a key. In the case of the performer, by determining which finger is depressing which key during the recording of the sensory cue information for the learning lesson, the proper finger and hand position for playing the piece of music can be relayed to the student by the application of the appropriate haptic sensory cue during the learning session. In the case of the student, by determining which finger is depressing which key during the learning session, the accuracy of the student's playing of the piece of music can be monitored. Thus, each finger of each hand has a corresponding digit conductive pad and wire system that enables a circuit to be completed between the fingers of the user (student or performer) and the individual keys of the digit/key detecting keyboard. As shown in the first keyboard image of the first measure shown in FIG. 15, a suspended chord can be played by the user's left hand. In this case, the cord consists of the G key below middle C key and the E key below middle C key. The C, G, and E keys are played respectively by depressing each key with the individual fingers of the users left-hand. In this case, the thumb plays the C key, the middle finger plays the G key and the pinky plays the E key. Which keys to be depressed by which fingers are determined by the finger-key circuits being completed during the recorded performance.

Figures 24, 25:
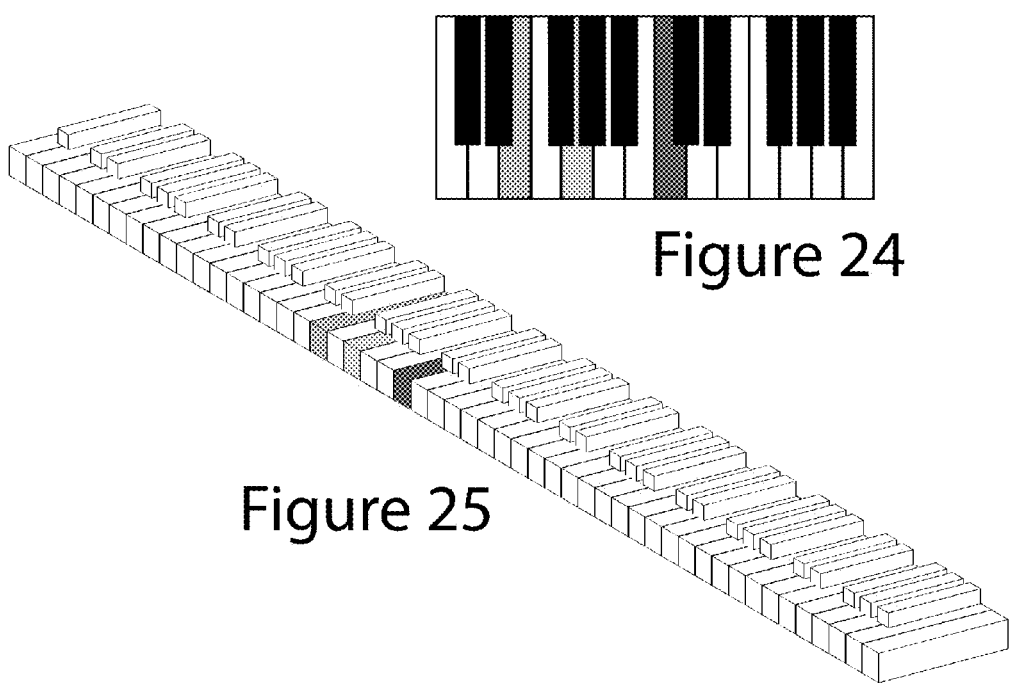
FIG. 24 illustrates one visual perspective of a keyboard that can be displayed to the student as a visual sensory cue.
FIG. 25 illustrates another visual perspective of the keyboard that can be displayed to the student as a visual sensory cue.

FIG. 24 illustrates one visual perspective of a keyboard that can be displayed to the student as a visual sensory cue. FIG. 25 illustrates another visual perspective of the keyboard that can be displayed to the student as a visual sensory cue. FIG. 26 illustrates yet another visual perspective of the keyboard that can be displayed to the student as a visual sensory cue, in this case the visual perspective corresponds to the viewpoint of the performer. During the learning session, or when the inventive system is used for entertainment purposes, etc., one or more visual perspectives can be displayed to the user. Alternatively, or additionally, other visual sensory cues can be displayed, including computer generated color coded images or other indicia of the device or performance object (such as, but not limited to, the objects described herein including a piano, guitar, remotely controlled drone, sports equipment, etc).

Figure 27:
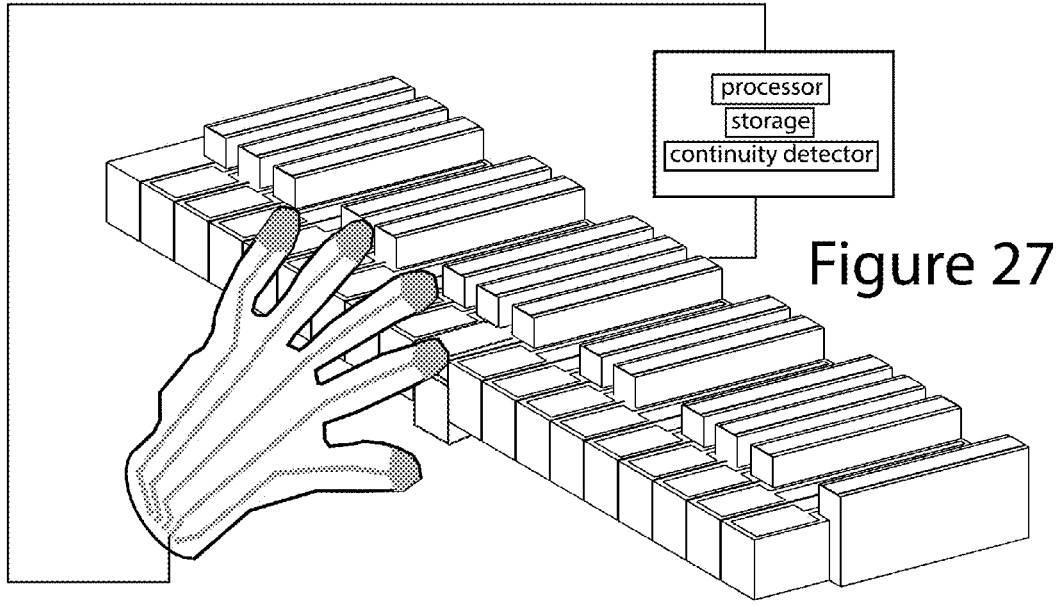
FIG. 27 illustrates a detection of a piano key being played, and a detection circuit illustrated as a block diagram including a processor, storage and continuity detector.

FIG. 27 illustrates a detection of a piano key being played, and a detection circuit illustrated as a block diagram including a processor, memory storage and electrical continuity detector. The velocity of the key or the volume of the note being played can also be recorded, and the intensity of the haptic and visual feedback can be adjusted in accordance with the auditory feedback so that a louder note has an increase haptic sensation and a brighter visual light cue. A body member position detector may comprise a first conductor associated with the body member of the performer and a second conductor associated with the performance element of the performance object. The conductive glove and the keyboard and detection circuit structure are an example of a mechanism for determining the position of a body member relative to a performance element of a performance object on which an event is to be performed. Other examples include a camera and pattern recognition software, or transducers, light detectors, proximity sensors, and the like. The mechanism includes a body member position detector that detects a position of a body member of a user relative to a performance element of a performance object with which an event is to be performed. For example, the body member position detector can be the conductive glove and the conductive elements on the keys of a keyboard as described by way of example herein. A first conductor can include a conductive member associated with a finger of the performer and second conductor can be a conductive surface associated with a key or a musical instrument. Then the first conductor contacts the second conductor a circuit is completed and the circuit continuity can be detected to indicate the body part and the key played by the body part. Alternatively, a video camera and computer running pattern recognition software can be used to detect the position of the body member relative to a performance element of a performance object with which an event is to be performed (e.g., fingers relative to the keys of a keyboard on which music is being played). A signal generator generates a signal dependent on the detected position of the body member (e.g., processor and continuity detector). A signal recorder records the signal so that at least one sensory cue can be determined to indicate the position of the body member relative to the element of the performance object during a learning session (e.g., processor and memory storage).

As shown in FIG. 27, the body member can be at least one of a hand and at least one finger of the performer. In this case, the event can be, for example, a piece of music to be performed on a musical instrument such as the keyboard, trumpet or guitar. The performance object is the musical instrument, and the performance element is at least one of a key, a string and a valve of the musical instrument. Alternatively, the body member can be another part of the user's body, such as the arms and shoulders, and the event can be a sporting activity, such as tennis. The performance object in this case would be a tennis racket and the position of the performance object can be detected by appropriate proximity sensor, motion detectors, tilt detectors, a laser positioning system, and other mechanisms used to detect the position of an object in three-dimensional space. The performance element in this case may be the handle of the tennis racket, and its position relative to a arm of the user as a tennis ball approaches and is struck by the racket can be determined. The tennis ball can be an actual tennis ball, or a computer generated tennis ball that the user sees and reacts to during a recording of the sensory cues that will be used to teach the performance. This mechanism and method for detecting and recording the position of body parts and performance objects/performance elements is used to record the sensory cues that are used to teach the event and build up memory associations of the event in the various processing centers of the student's brain. The body member that is detected during the recording of the event performance and then stimulated during the learning lesson or entertainment session can be at least one of a finger, toe, hand, foot arm, leg, shoulder, head, ears and eyes of the user. This technique of using the inventive accelerated learning system can be used, for example, to create a virtual sport video game. Similar alternatives can be constructed for other events, such as controlling a remotely controllable system, for example, the flying of a drone airship, a space exploration probe, the playing of a guitar, the assembly of a weapon, entertainment or brain rehabilitation to help "rewire" the brain of a stroke victim or brain damaged patient, other cognitive therapy including enhanced learning, or any other event where a user can benefit from recorded sensory cues that stimulate the various processing centers of the brain.

Figure 28:
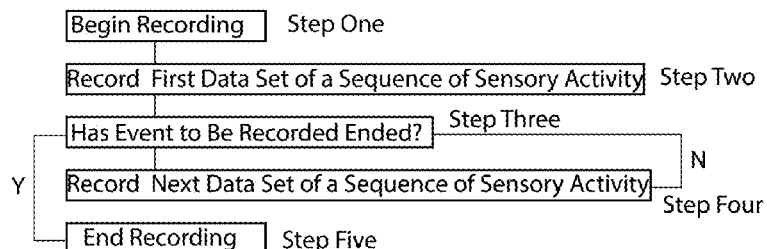
FIG. 28 is a flow chart illustrating the steps for recording data sets of a sequence of sensory activity of an event to be recorded. The recorded data can be an actual recording made from a real world action, such as a piano key being played, or the recorded data can be a determined from a computer program code so that data sets of a sequence of sensory activity can be recorded.
Figure 29:
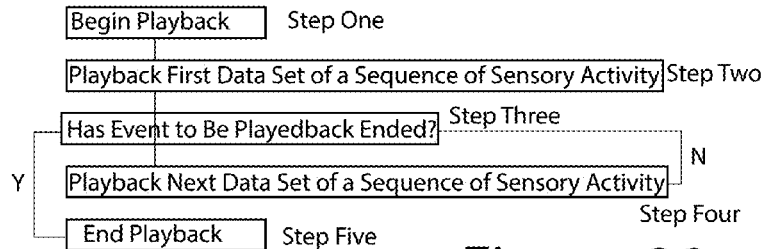
FIG. 29 is a flow chart illustrating the steps for playing back data sets of a sequence of sensory activity of an event that has been recorded. The played back data can be a recording of actual performance made from a real world action, such as a piano key being played, or the played back data can be determined from a computer program code so that data sets of a sequence of sensory activity can be played back.

FIG. 28 is a flow chart illustrating the steps for recording data sets of a sequence of sensory activity of an event to be recorded. The recorded data can be an actual recording made from a real world action, such as a piano key being played, or the recorded data can be determined from a computer program code, or a combination of real world recorded data and computer generated data, so that data sets of a sequence of sensory activity can be generated during a learning session. FIG. 29 is a flow chart illustrating the steps for playing back data sets of a sequence of sensory activity of an event that has been recorded. The played back data can be a recording of actual recording made from a real world action, such as a piano key being played, or the played back data can be a determined from a computer program code so that data sets of a sequence of sensory activity can be played back.

Figure 30:
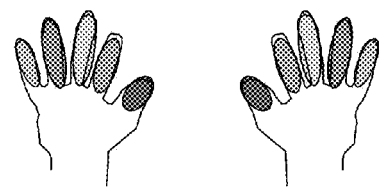
FIG. 30 schematically shows a potential color coding of the fingers or digits of a user in accordance with the inventive accelerated learning system.
Figure 31:
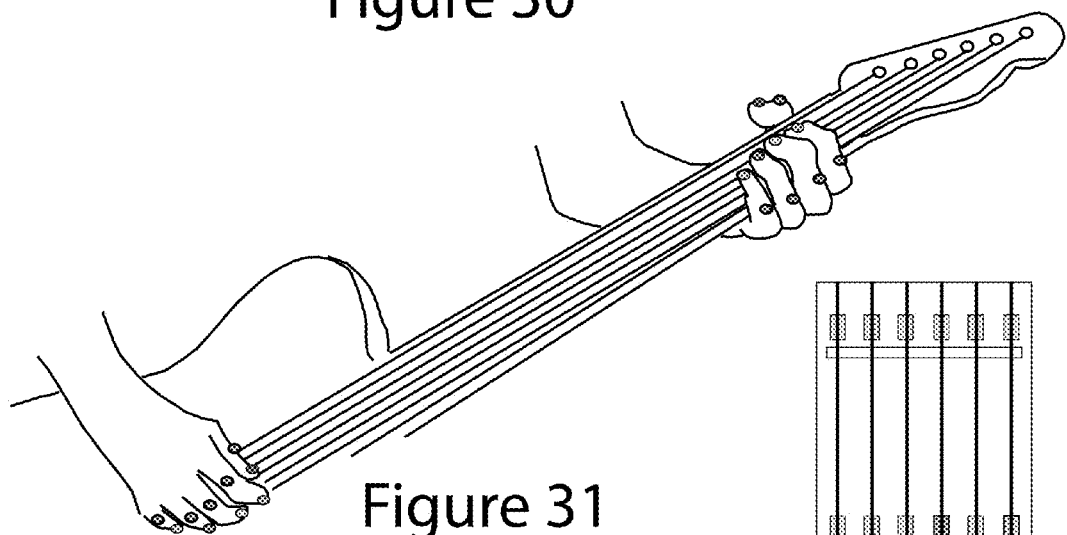
FIG. 31 shows a guitar being played in accordance with the inventive accelerated learning system, the fingers of the user having color coded lights for providing visual sensory information and vibrators disposed on the fingers of the user for providing haptic sensory information.
Figure 32:
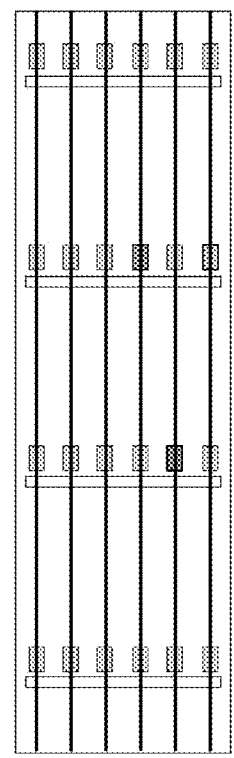
FIG. 32 illustrates a portion of the neck of a guitar constructed in accordance with an embodiment of the inventive accelerated learning system, with an indication of the strings to be played by the user corresponding to the color coding on the users fingertips.

FIG. 30 schematically shows a potential color coding of the fingers or digits of a user in accordance with the invented accelerated learning system. FIG. 31 shows a guitar being played in accordance with the inventive accelerated learning system. The fingers of the user having color coded lights for providing visual sensory information and vibrators disposed on the the fingers of the user for providing haptic sensory information. FIG. 32 illustrates a portion of the neck of a guitar constructed in accordance with an embodiment of the inventive accelerated learning system, with an indication of the strings to be played by the user corresponding to the color coding on the users fingertips. The neck of the guitar can have color lights at each fret associated with each string. An RGB combination LED can be used so that a wide range of perceived colors can be generated at each light. The colors match the color code learned by the user to indicate.

Figure 33:
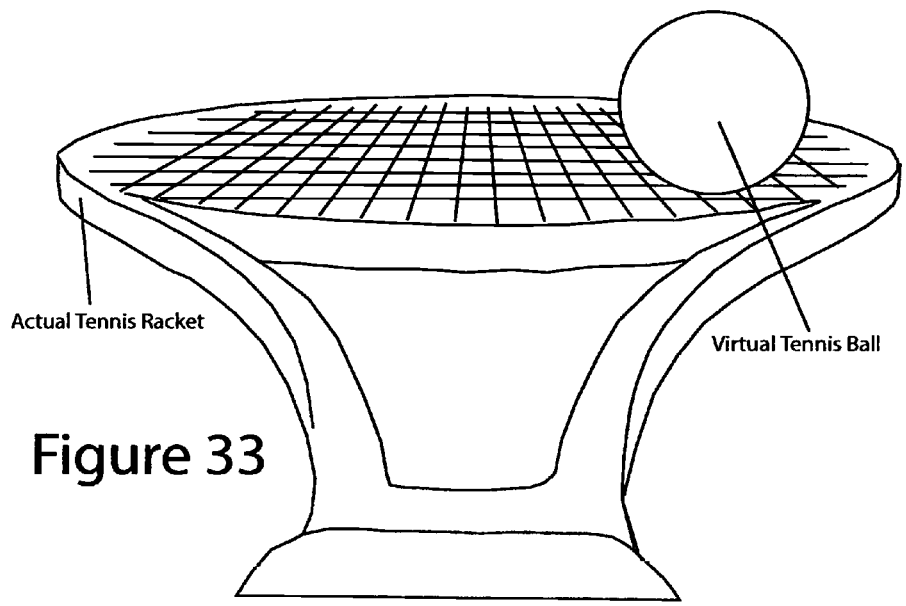
FIG. 33 illustrates a visual sensory cue showing an actual tennis racket seen from the perspective of the user with an overlay of a virtual tennis ball generated using computer program code and displayed using an augmented reality display, such as augmented reality eyeglasses.

FIG. 33 illustrates a visual sensory cue showing an actual tennis racket seen from the perspective of the user with an overlay of a virtual tennis ball generated using computer program code and displayed using an augmented reality display, such as augmented reality eyeglasses. Eye-hand coordination for playing tennis can be taught using an embodiment of the inventive accelerated learning system. In this case, the visual sensory cue can be the tennis ball coming towards the user, and the head movement to bring the ball into the racket. The haptic sensory cues can be electrical impulses applied to the muscles of the arm to strike the ball with the racket. Also, impulses can't be provided to the muscles controlling head movement. Also, shoulder and back movement, and various other muscles that are major factors in positioning the racket to strike the ball.

Figure 34:
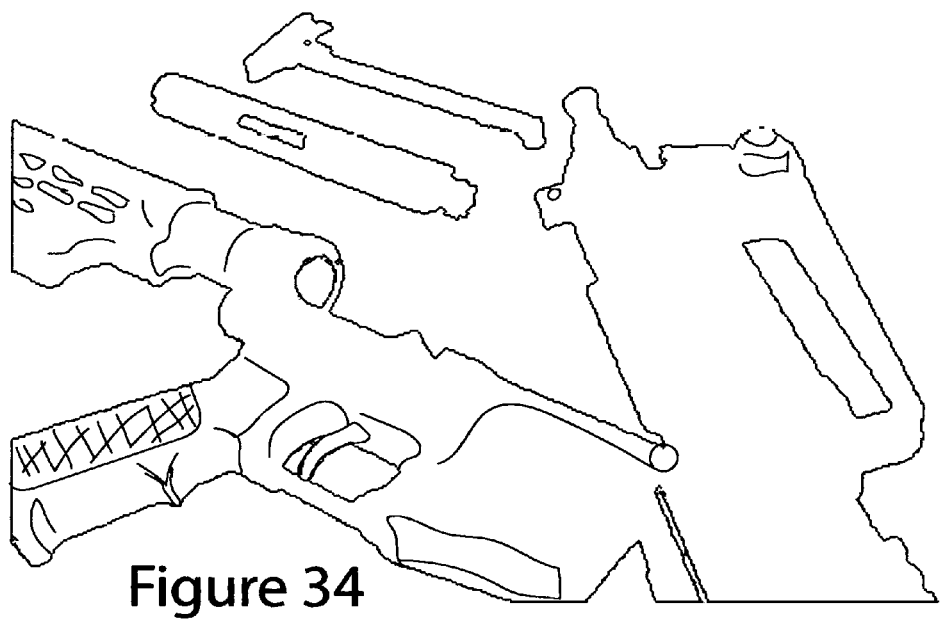
FIG. 34 shows a disassembled military firearm illustrating an application of the inventive accelerated learning system for military use.

FIG. 34 shows a disassembled military firearm illustrating an application of the inventive accelerated learning system for military use. The military use can be the assembly of a weapon. In this case, the perspective can be from a soldier assembling a disassembled weapon, and the determined haptic sensory cues can be the muscle groups used to pick up and assemble the pieces of the weapon. For the haptic stimulation, electrical impulses can be synchronized to the visual cues.

Figure 35:
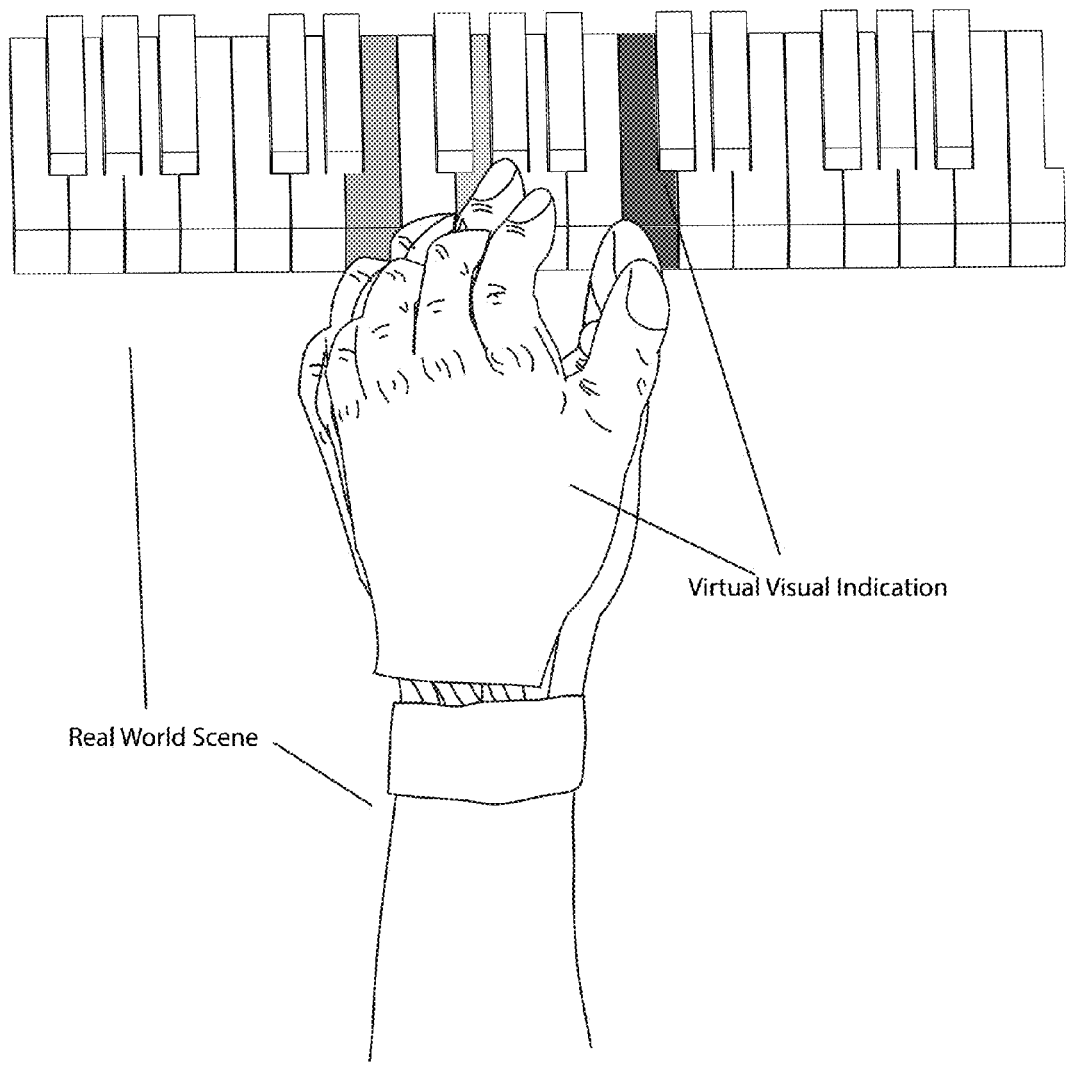
FIG. 35 illustrates a visual sensory cue showing an actual piano and the user's hand seen from the perspective of the user with an overlay of a hand generated using computer program code or from a recorded image and displayed using an augmented reality display, such as augmented reality eyeglasses.

FIG. 35 illustrates a visual sensory cue showing an actual piano and the user's hand seen from the perspective of the user with an overlay of a hand generated using computer program code and displayed using an augmented reality display, such as augmented reality eyeglasses.

Figure 36:
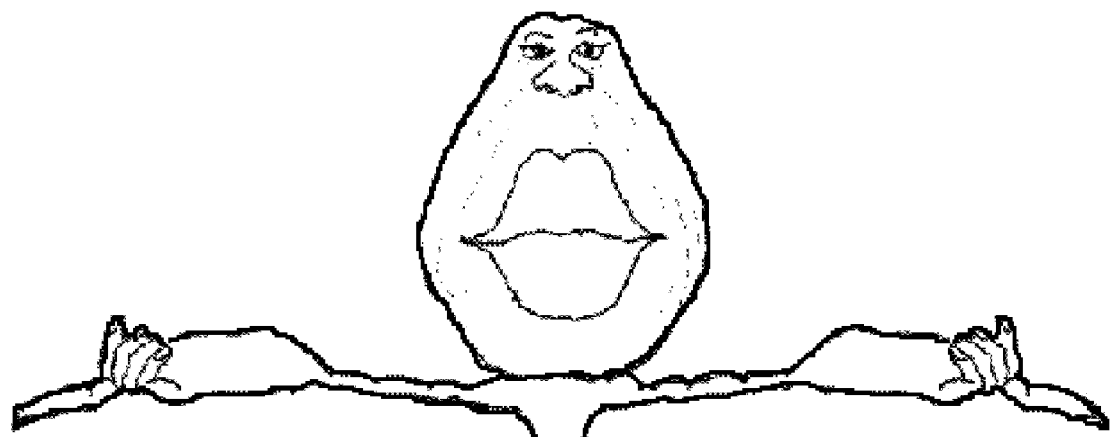
FIG. 36 shows the proportional nerve endings on the human body.

FIG. 36 shows the proportional nerve endings on the human body. As can be seen, the hands of a human are particularly sensitive to haptic stimulation. For example, the muscles that move the finger joints are in the palm and forearm. Muscles of the fingers can be subdivided into extrinsic and intrinsic muscles. The extrinsic muscles are the long flexors and extensors. They are called extrinsic because the muscle belly is located on the forearm. The application of haptic sensation, such as the haptic sensory cues, can be applied to various parts of the body, and the inventive accelerated learning system adapted to enable a wide range of applications, from teaching to entertainment to rehabilitation. By noting the sensitivity to stimulation as indicated in FIG. 36, the application of haptic sensory cues can be selective in accordance with a desired learning or entertainment enhancement. For example, the fingers (and/or the muscles controlling the fingers and/or the nerves communication with those muscles) can receive haptic stimulation in the form of a pressure, vibration, electrical impulse or other stimulation. As described herein, by thus stimulating the fingers, etc., a student can receive remote and active (at the instrument) accelerated learning.

Figure 37:
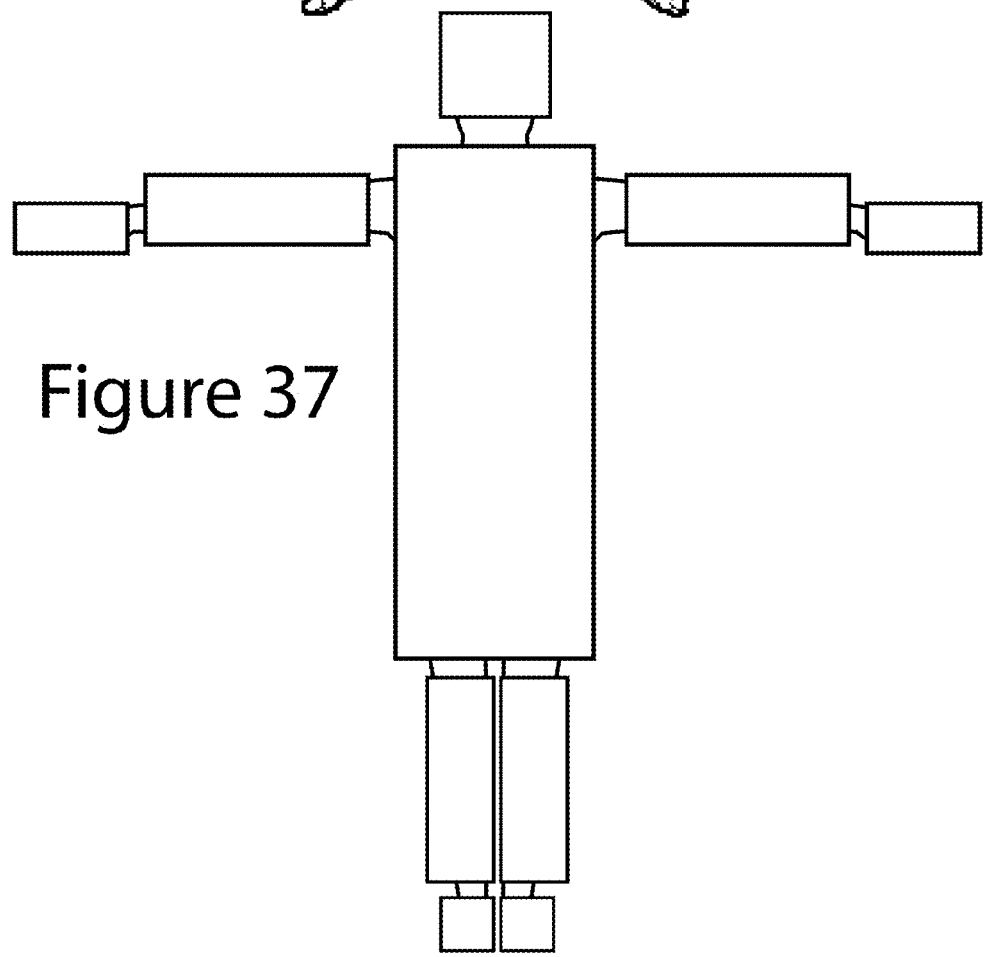
FIG. 37 illustrates a full body zoned haptic sensory stimulation system.

FIG. 37 illustrates a full body zoned haptic sensory stimulation system, which may take guidance in placement, type of stimulation, intensity and duration from the proportional nerve ending of the human body. The inventive accelerated learning system can include full body stimulation. Since the fingers are particularly sensitive, an example is application of an entertainment aspect of the present invention includes haptic stimulation applied as in a learning session to the user's fingers, while other haptic stimulation is applied to other parts of the body, while the music is being played and possibly a corresponding video image (computer generated or actual recorded).

Figure 38:
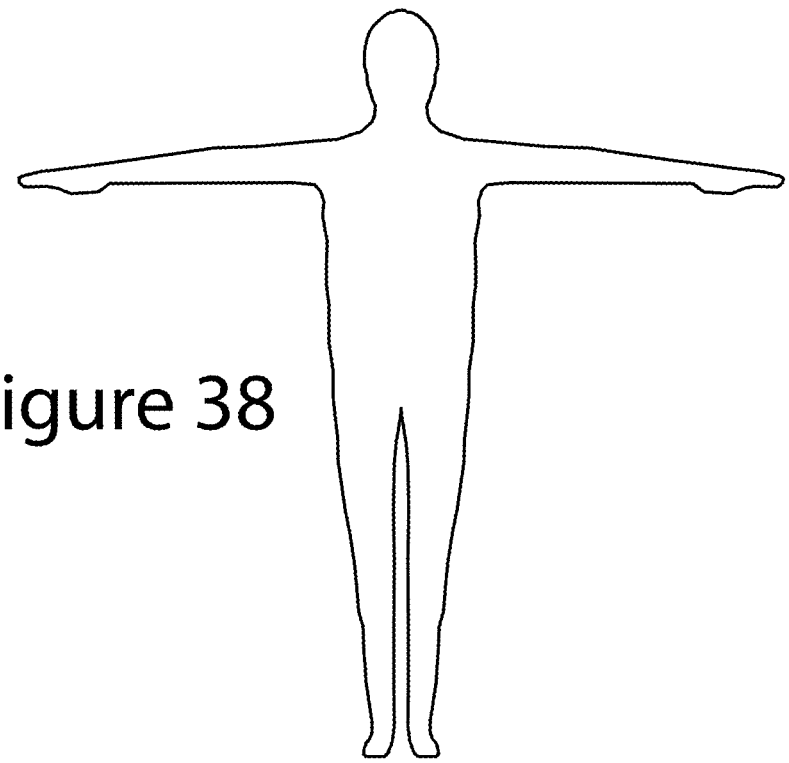
FIG. 38 illustrates a pilot of a remotely controlled drone aircraft.
Figure 39:
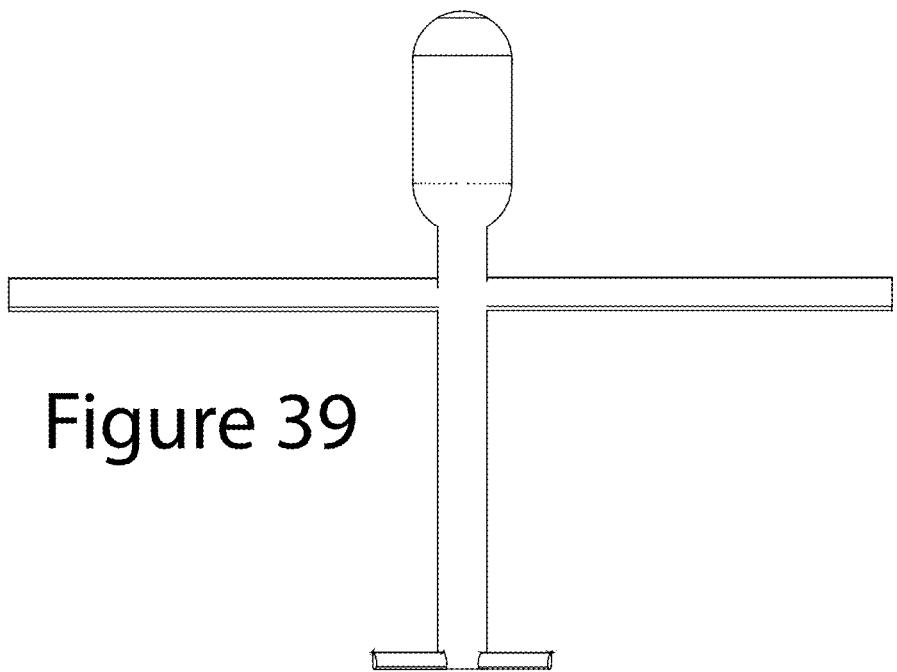
FIG. 39 is a top view of a remotely controlled drone aircraft.
Figure 40:
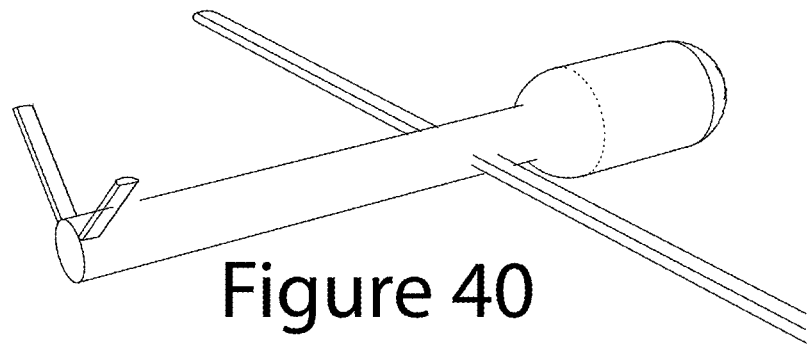
FIG. 40 is a side perspective view of a remotely controlled drone aircraft.
Figure 41:
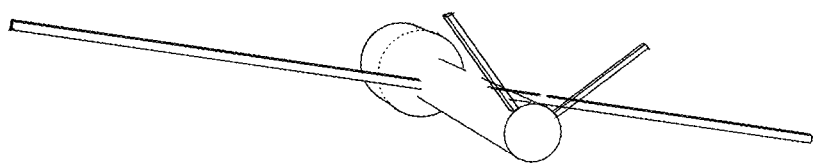
FIG. 41 is a back perspective view of a remotely controlled drone aircraft.
Figure 42:
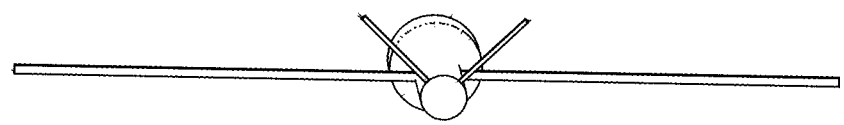
FIG. 42 is a rear view perspective of the remotely controlled drone aircraft.
Figure 43:
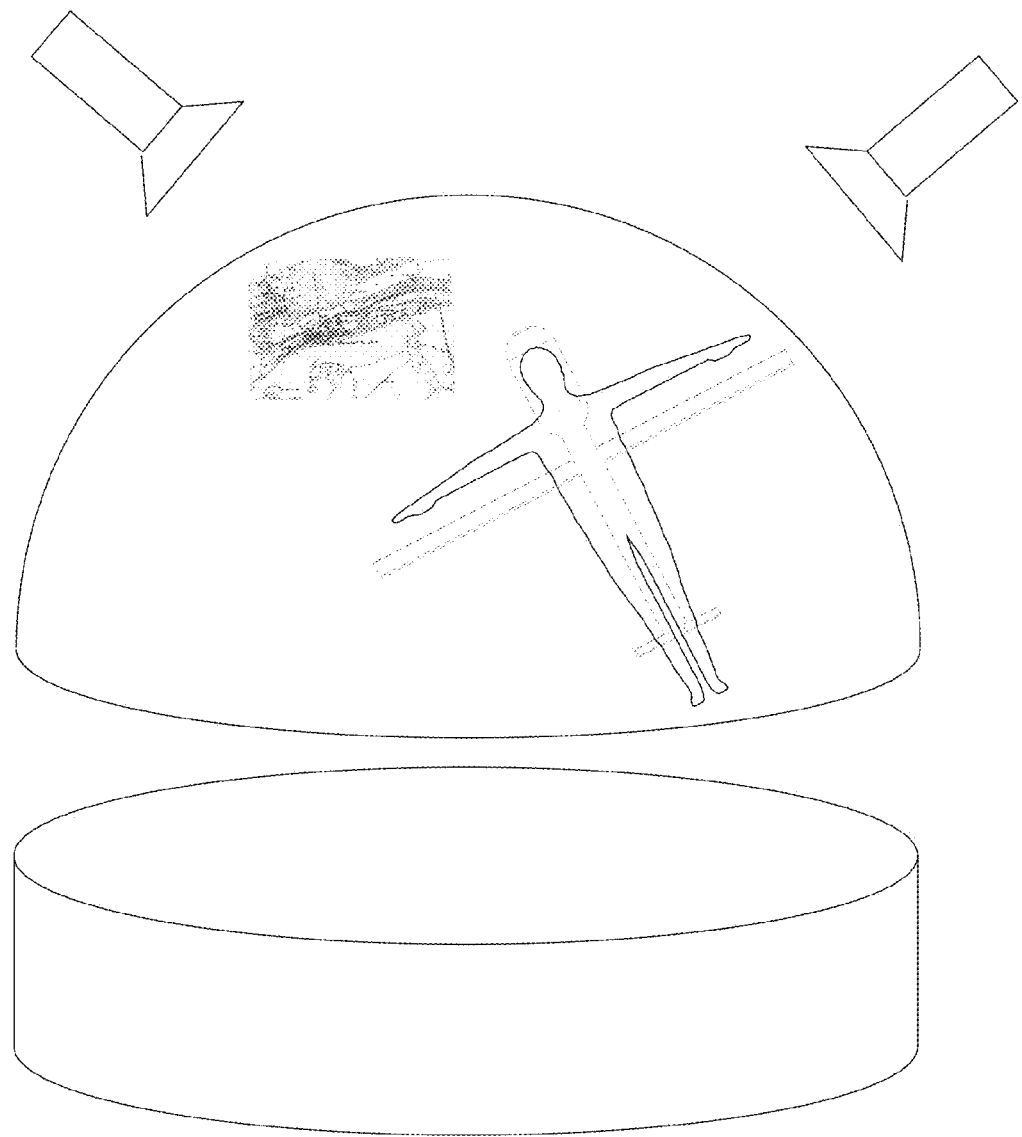
FIG. 43 illustrates an isolation chamber and video projection dome in accordance with an aspect of the inventive accelerated learning system.
Figures 44, 45:
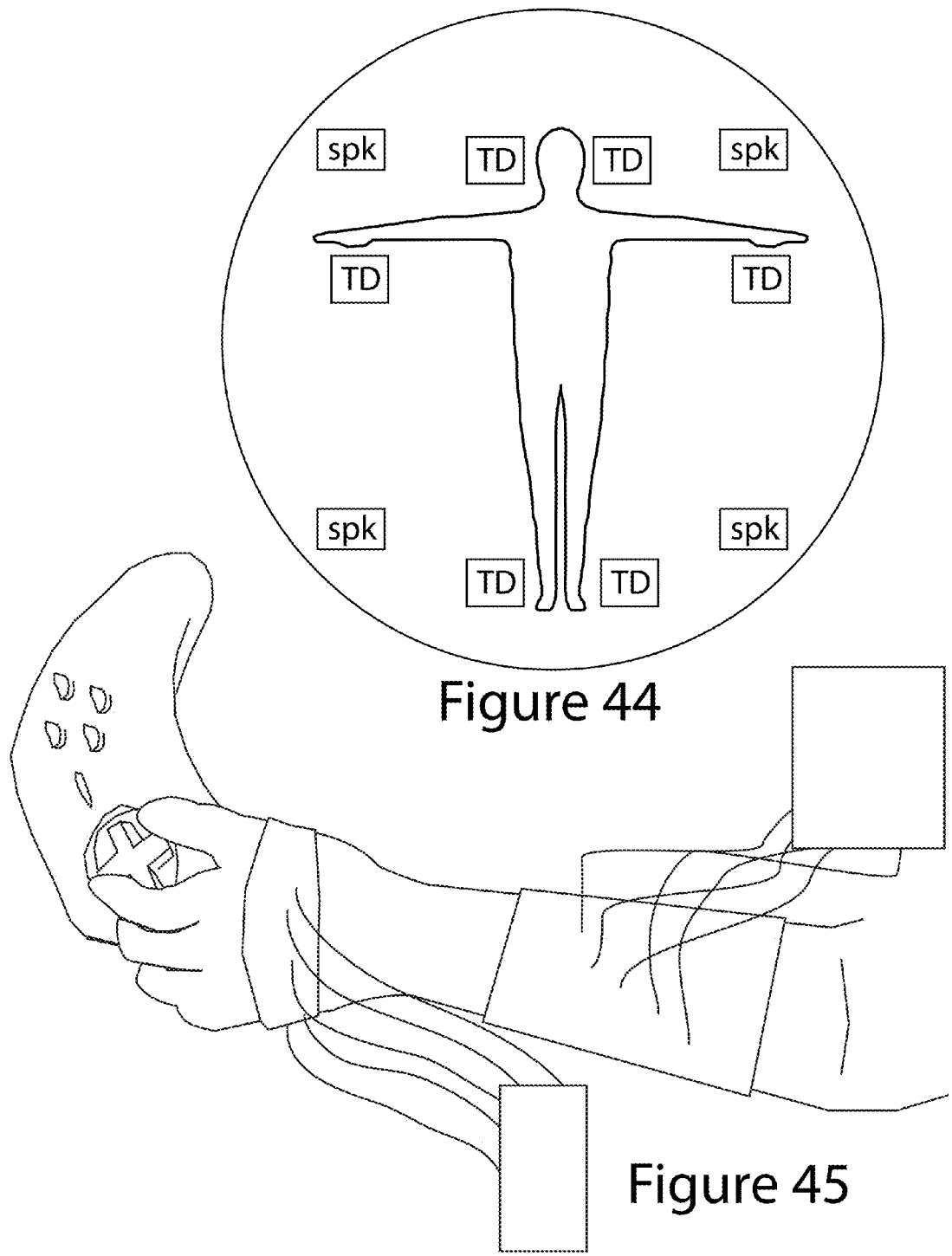
FIG. 44 illustrates a user in the isolation chamber showing transducers for determine the position of parts of the user's body and an above and below water surround sound speaker system for providing audio sensory cues.
FIG. 45 illustrates a use of the inventive accelerated learning system for teaching and/or improving hand-eye coordination for a control device such as a joystick, remote control unit and/or video game controller.

FIG. 38 illustrates a pilot of a remotely controlled drone aircraft. FIG. 39 is a top view of a remotely controlled drone aircraft. FIG. 40 is a side perspective view of a remotely controlled drone aircraft. FIG. 41 is a back perspective view of a remotely controlled drone aircraft. FIG. 42 is a rear view perspective of the remotely controlled drone aircraft. FIG. 43 illustrates an isolation chamber and video projection dome in accordance with an aspect of the inventive accelerated learning system. FIG. 44 illustrates a user in the isolation chamber showing transducers for determine the position of parts of the user's body and an above and below water surround sound speaker system for providing audio sensory cues. This embodiment of the inventive accelerated learning system takes advantage of sensory deprivation to intensify the brain associations made from the simultaneous sensory cues. The sensory deprivation chamber reduces the brain's processing of external stimuli and provides a comfortable and relaxing experience for the user. The administering of appropriate chemicals, such as nootropic or neurotropic drugs, can further enhance the positive aspects of the inventive system, such as the ability of the operator to learn during the learning session or a patient to recover brain function through the "re-wiring" of the brain after injury or degradation.

The inventive accelerated learning system can be used to teach and/or improve hand-eye coordination for a variety of activities, including, but not limited to, video and online gaming, as well as remote control of devices, such as military drones and the like.

In the case of military drones, it is desirable that the operators be given much time at the controls of the remote drone in order to learn the subtleties of remote controlling a drone or robot. For example, in the case of a flying drone, the operators can be provided with a flight simulation so that the cost and time involved in flying an actual drone is avoided. The operator can also be given a more immersive experience without having to fly the actual drone. In this case, the operator may use a recorded actual drone mission, and receive haptic, visual and audio cues that replicate the experience of the remote drone operator during the actual mission. The actual mission can include a predetermined course, so that the operator knows what to anticipate before the haptic audio and visual cues are applied. For example, the set course may include a series of banking and turning maneuvers and/or take off and landing.

The inventive accelerated learning system may be particularly useful for military instruction. For example, as military technology progresses, there is an increasing emphasis on the use of remote control devices, such as robots and drones to replace operators and soldiers and other military personnel in the field.

Robot and drone use is becoming increasingly advantageous for other applications, such as law enforcement. Further, it is likely that civilian entertainment and other uses will become more and more dependent on the remote control of devices. Also, remote exploration such as deep-sea and space exploration will increasingly rely heavily on remote sensing/control of robotic systems.

The drones can be equipped with sensors, so that real time telepathy of motions and other sensory cues such as vibrations caused by wind gusts or banking of the drones wings, can be translated into haptic sensory cues applied to the remote drone operator.

The sensory cues translated from sensors on board the drone can also be applied as audio and/or visual cues. Thus, the remote drone operator is able to perceive different aspects of the drone flight performance through various sensors and sensory cues. Because the different sensory cues are stimulating different parts of the operator's brain, the operator is able to process the information in a manner which may be more optimal then if the operator were to simply feel, for example, a rumble-pack type vibration simulating the buffeting of the drone caused by wind currents. That is, the onboard vibration, or banking, acceleration, etc., experienced by the drone can be sensed using onboard sensors, and the telepathy of those sensors received and used to provide sensory stimulation to the remote drone operator. The sensory stimulation may be, as just one example, audio and visual cues applied to the operator to stimulate various parts of the operator's brain as an indication of the drone's performance. Through consistent combined sensory stimulation, the operator receives enhanced learning of the subtleties of the drones performance in relation to external factors, such as wind, altitude and air temperature, and the operator's control. For example, if the operator's control would result in a stall, an onboard tilt sensor can provide telepathy indicating that the wing of the drone has an angle of attack that will result in an imminent stall. This telepathy can be converted into an audio and visual warning to indicate to the operator that a corrective action should be taken to prevent the stall.

More than just receiving an audio and visual warning, in accordance with the inventive accelerated learning system, these sensory cues can be received in addition to haptic cues and electrical impulses applied to one or more area of the operator's body, to create a strong learned behavior/skills reinforcement in a highly immersive and convenient manner.

FIG. 44 illustrates a user in the isolation chamber showing transducers for determine the position of parts of the user's body and an above and below water surround sound speaker system for providing audio sensory cues.

The remote control of a flying drone is an example of a use of an embodiment of the inventive accelerated learning system. A plurality of first sensory cues are generated capable of being perceived by a user. Each first sensory cue of the plurality of first sensory cues is dependent on a position of at least one body member of a performer relative to a performance element of a performance object with which an event is performed. In this case, the performer can be an actual pilot of a drone aircraft and the actual pilot's responses and control of the remotely controllable drone can be recorded to provide the sensory cues to the user (e.g., a student pilot). Alternatively, artificial intelligence can be used to determine how a virtual pilot would react, for example, in a combat, take off, landing, or poor weather situation, and in this case the performer is a computer generated virtual performer. Whether they are dependent on an actual performer or a virtual performer, when perceived by the user, the plurality of first sensory cues are effective for stimulating a first processing center of a brain of the user. For example, in the case of the flying of a drone aircraft, the position of the hands, fingers and/or feet of the actual or virtual pilot can be determined relative to a joystick, buttons and/or other controllers of the remote controller used to perform the event of actually or virtually flying the drone.

A plurality of visual sensory cues capable of being displayed to the user on a video display device are also generated. For example, the visual sensory cues can be dependent on signals from a video camera on an actual drone, or dependent on computer generated video images. The visual sensory cues provide a virtual visual indication to the user of the position of the at least one body member. For example, the virtual visual indication can be the reaction of the drone to the body member position, and/or they can be the position of the actual or virtual performers body member relative to the controls. As described elsewhere herein, two or more images can be display simultaneously to the user either as an overlay (one image over the other) or side by side. The visual sensory cues are effective for stimulating the visual processing center of the brain of the user. The visual sensory cues are synchronized with the first sensory cues so that the position of the at least one body member is virtually visually indicated in synchronization with the first sensory cue and so that the visual processing center is stimulated with a visual sensory cue in synchronization with a first sensory cue stimulating the first processing center. The synchronized stimulation of the first processing center and the visual processing center is effective for teaching the user to perform a version of the event. That is, the user receives the sensory cues related to the actual or virtual performed event, and these sensory cues are effective to create memory associations in the brain of the user so that the user learns how to perform a version of the event.

A second plurality of sensory cues capable of being perceived by the user can also be generated. Each second sensory cue of the plurality of sensory cues is dependent on at least one of the position of the at least one body member and an action of the event. The action dependent on the position of the at least one body member. In other words, as an example, the action in this case can be how the remotely controlled drone reacts to the position of the hand gripping the joystick that controls the drone. The second sensory cues are effective for stimulating at least a second processing center of the brain of the user. The second sensory cues are synchronized with the first sensory cues so that the second processing center is stimulated with a second sensory cue in synchronization with a first sensory cue stimulating the first processing center. The synchronized stimulation of the first processing center, the visual processing center and the second processing center is effective for teaching the user to perform a version of the event. For example, haptic or electrical stimulation can be used as the second plurality of sensory cues. In this case, the muscles and/or nerves that control the muscles are stimulated corresponding to the position of the body member(s) or the actual or virtual drone pilot. As an example, if during a real combat mission an actual pilot of a drone is forced to deploy a weapon in reaction to a visual indication provided from the drone camera, and/or an audible command indicating hostile forces are acting against friendly troops the drone is protecting, the actual pilots reaction to the visual indication and/or command can be provided along with the same visual indication/command to the student pilot so that the student pilot learns during a training exercise of the correct response against the hostile forces needed to protect the troops.

The video display device can comprise at least one of pair of augmented and/or virtual eyeglasses, a computer monitor, a television, a smart phone display or a personal information device display. For example, in the case of the eyeglasses, a device such as google glass can be used to record the body member position of the actual pilot during the actual drone flight, providing that pilots perspective and indicating when he looks down at his hands, up at a display screen or instrument, and even what portion of the screen or instrument or what screen or instrument is viewed during the reaction to a particular flight situation. The user during the learning session is then given the same visual information in the form of the virtual visual cues. The muscles and/or nerves that control the movement of the head and even the muscles controlling the movement and focus of the eyes can be stimulated in synchronization to the visual cues so that the muscle memory is created in the association among the different brain processing centers.

As described herein, and as will be logically foreseeable to one ordinarily skilled in the art from the teachings herein, the event can be many different activities and actions, including controlling at least one of a sports related object, a musical instrument, a weapon, a video gaming controller, a remotely controllable system including a space probe, a drone aircraft, an underwater probe, a robot. Also, at least one of the first and the second plurality of sensory cues are remotely determined from corresponding to the event that is performed, the event being remote in at least one of time and location relative to the user; and wherein at least one of the first and the second plurality of sensory cues stimulates a brain processing center for at least one of the five senses of hearing, seeing, smelling, feeling and taste.

The flight controls, for example, controlling a drone can be enhanced beyond the conventional joystick operation. For example, the drone operator can be placed into a sensory deprivation tank, and an intuitive control of the drone can be accomplished using for example, the detection of the position of outstretched arms of the user. As an example, by controlling the rotation of the hand, such as one might do when driving down the road with the hand out the window, the wing control surfaces can be remotely actuated to enable the operator to intuitively control the drone. Further, for entertainment, learning, therapeutic, military and/or other functional use, the operator can be given a highly immersive illusion of real flight. Since the drone operator is in the sensory deprivation tank, his or her brain will be more receptive to the sensory cues that are applied. Thus, for example, a widescreen, or eyeglass, display can be used to provide visual cues. As illustrated in FIG. 43, a translucent dome over the sensory deprivation tank or chamber can be used as a projector screen, and the various perspectives of the drone (some of which are shown in FIGS. 39-42), along with other data (such as a map) can be made visible to the operator in the tank. As with the embodiment described herein for teaching music, image overlays, color coding, etc., can be utilized to provide single or simultaneous visual sensory cues. Speakers, or head phones can be used to apply the auditory sensory cues. Further, proximity sensors or transducers and an appropriate array of transmitters and/or receivers used to determine the position and rotation of the drone operators hands, or other appendages including the position of the head, eyes, feet and legs.

FIG. 45 illustrates a use of the inventive accelerated learning system for teaching and/or improving hand-eye coordination for a control device such as a joystick, remote control unit and/or video game controller. In the case of a gaming controller, for example, shown in FIG. 45, the typical haptic feedback may be applied in addition to the haptic sensory cues provided by the inventive accelerated learning system. For example, the rumble pack of a video game can be used to provide further sensory information during the learning exercise. In this case, the rumble pack may be simulated by an additional vibrator disposed in the palm of the haptic gloves. In accordance with an embodiment of the inventive accelerated learning system, a drone operator can be placed, for example, into a sensory deprivation chamber, during the learning sessions and/or during actual troll drone flights. The nerve endings and muscles of the user can be stimulated by vibration or electrical impulse. Also, the electrical impulses traveling on the nerves and the muscle movements in response to those impulses can be detected to record a performance for a learning session, and/or to detect that the student is correctly applying the learned skill or behavior, and/or to provide cognitive and physical therapy.

Figure 46:
FIG. 46 illustrates color coding for bass, midrange and high range audio sensory cues.
Figure 47:
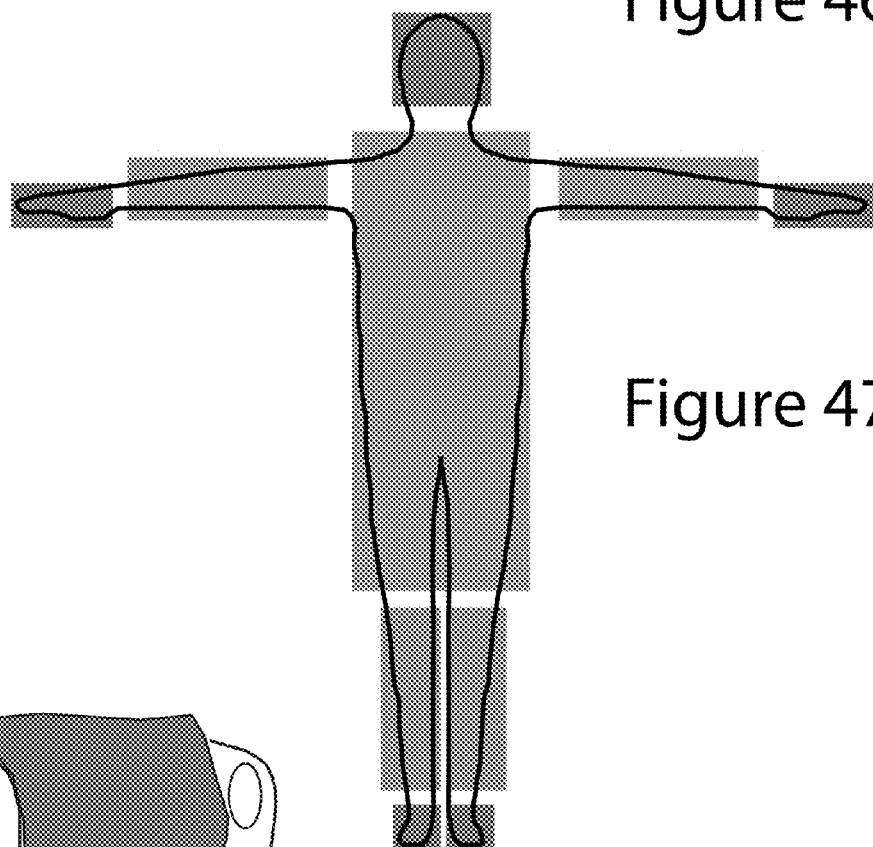
FIG. 47 illustrates the color coding of the audio sensory cues mapped to a human body.
Figure 48:
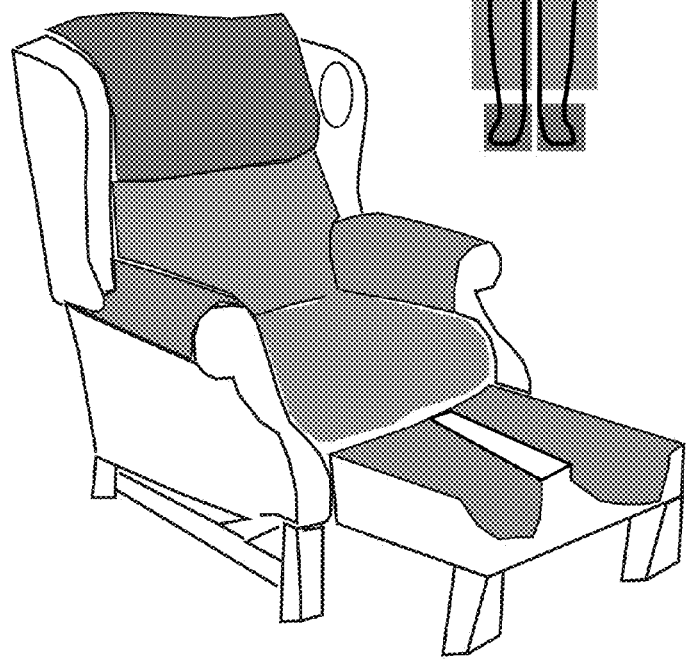
FIG. 48 illustrates a massage chair having zones corresponding to the color coding shown in FIG. 45.

FIG. 46 illustrates color coding for bass, midrange and high range audio sensory cues. The bass, for example, can be applied as a massage, vibration, electrical signal and/or other haptic stimulation to the trunk of the body including, for example, the shoulders, back, buttocks and/or thighs. The mid-range can be applied as a massage, vibration, electrical signal and/or other haptic stimulation to the neck, arms and/or calves. The high-range can be applied as a massage, vibration, electrical signal and/or other haptic stimulation to the fingers, toes, head and/or face. FIG. 47 illustrates the color coding of the audio sensory cues mapped to a human body The haptic, electrical, etc., stimulation can be applied through devices positioned in communication with various locations of the users body. The haptic sensory cues can be mapped to a chair, bed, clothing or apparatus that can be worn by the user. FIG. 48 illustrates a massage chair having zones corresponding to the color coding shown in FIG. 45. For example, in the case of a massage chair, a soothing massage can be applied wherein the massage to various parts of the body are mapped to the different frequencies of a piece of music. The sensory cues can also include other senses, such as taste and smell. In this case, the senses of taste and/or smell can be utilized to provide positive and negative reinforcement of a learned activity. For example, in the case of a drone operator learning to determine how to recognize friend or foe, during a training exercise a visual sighting that challenges the operator with making a correct snap determination of friend or foe can be reinforced by providing a pleasant smell when a correct determination is made and an unpleasant smell when an incorrect determination is made. By this application of additional sensory cues as reinforcement to learned behavior or responses, another processing center of the brain is brought into the combined sensory processing learning experience. The different ranges of music frequency can also be mapped to visual stimulation in the form of light colors. The light colors can correspond, for example, to the sensitivity of the human eye to color stimulation. Thus, for example, the color can be generated by LED lights that match the peak wavelength sensitivity of the cones of the human eye. The three types of cones have peak wavelengths near 564-580 nm, 534-545 nm, and 420-440 nm, respectively.

A few other applications of the inventive accelerated learning system include:

Rehabilitation Device:

The present invention can be used as a rehabilitation device, for example, to induce movement in the individual fingers on a hand. That is, the muscles that control movement of each finger can be separately targeted.

In accordance with the present invention, multiple sensory cues are simultaneously received by a patient, such as a stroke victim. For example, audio (musical tones), visual (displayed hand position on a keyboard) and haptic (vibration applied to individual fingers corresponding to notes being played) can be used to "teach" a patient how to play a simply song on a piano keyboard. By providing the simultaneously applied multiple sensory cues, the goal is to strengthen the patient's brain and nervous functions that control hand movement. In addition, or as an alternative, to the vibration received by each finger, the electrical stimulation of the nerves that control the individual finger movement can also be targeted. In accordance with an embodiment, the nerve stimulation is applied in a more general way (e.g., stimulate the middle and ring finger simultaneously) while applying the haptic sensation to only the individual targeted finger (e.g., the ring finger).

Stroke Victims

In accordance with the inventive accelerated learning system, a stroke victim or other brain injury or deficiency victim may acquire more rapid rerouting or rewiring of the various communication signals between areas of the brain. For example, if the portions of the brain related to auditory processing are damaged or otherwise defective, the visual and sensory cues, along with the audio cues, generated to stimulate the various processing centers of the brain of the stroke victim will help to reinforce newly learned auditory responses as the brain rewires those specific portions related to auditory processing.

Spinal Cord or Nerve Damage

The inventive accelerated learning system can be used to enhance the rehabilitation of spinal cord and/or nerve damage patients. In this case, the haptic stimulation in conjunction with the auditory and visual stimulation or sensory cues will enable a nerve and or spinal cord damaged patient to begin the association of the sense of touch with the audible and visual sensory cues.

The invention claimed is:

1. An apparatus, comprising:
   at least one processors; and
   at least one memory including computer program code,
   the at least one memory and the computer program code configured to, with the at least one processor, cause the apparatus to perform at least the following;
   detect a change in position of a body member of a performer relative to a performance element of a performance object with which an event is to be performed;
   generate a signal dependent on the detected change in position of the body member;
   record the signal so that a first sensory cue can be determined to indicate the change in position of the body member relative to the element of the performance object during a learning session;
   determine the first sensory cue dependent on the recorded signal; and
   apply the first sensory cue to indicate to a user during the learning session the change in position of the body member of the performer during the performance of the event, the first sensory cue being effective for stimulating a first processing center of a brain of the user,
   wherein the first sensory cue is an applied electrical signal dependent on the recorded signal effective to stimulate at least one of muscles and nerves of the user during the learning session to indicate to the user the position of the body member of the performer during the performance.

2. An apparatus according to claim 1; wherein the body member is at least one of a hand and at least one finger of the performer; and wherein the event is piece of music to be performed on a musical instrument, the performance object is the musical instrument and the performance element is at least one of a key, a string and a valve of the musical instrument.

3. An apparatus according to claim 1: wherein the change in position of the body member is detected from electrical impulses received from the body member.

4. An apparatus according to claim 1:
   wherein the at least one memory and the computer program code are configured to, with the at least one processor, cause the apparatus at least to further:
   record, during the performance of the event, at least one of haptic, auditory and visual data related to the performance of the event;

determine at least a second sensory cue dependent on the recorded at least one of haptic, auditory and visual data; and apply, during the learning session, the at least said second sensory cue synchronized with the application of the first sensory cue effective for stimulating at least a second processing center of the brain of the user.

5. An apparatus according to claim 1: wherein the applied electrical signal causes a sensation or contraction in the muscles of the user.

6. An apparatus according to claim 1: wherein the at least one memory and the computer program code configured to, with the at least one processor, cause the apparatus to further perform; detect electrical impulses of the user during the learning session.

7. A method, comprising:
detecting a change in position of a body member of a performer relative to a performance element of a performance object with which an event is to be performed;
generating a signal dependent on the detected change in position of the body member; and
recording the signal so that a first sensory cue can be determined to indicate the change in position of the body member relative to the performance element of the performance object during a learning session;
determining the first sensory cue dependent on the recorded signal; and applying the first sensory cue to indicate to a user learning session the learning session the change in position of the body member of the performer during the performance of the event,the first sensory cue being effective for stimulating a first processing center of the user; wherein the
first sensory cue is one of a haptic, auditory and visual sensory cue effective for stimulating a first processing center of a brain of the user; and
generating a visual sensory cue capable of being displayed to the user on a video display device, the visual sensory cue providing a virtual visual indication to the user of the change in position of the body member of the performer during the performance, the visual sensory cue being effective for stimulating the visual processing center of the brain of the user, the visual sensory cue being synchronized with the first sensory cue so that the change in position of body member of the performer is virtually visually indicated in synchronization with the first sensory cue and so that the visual processing center is stimulated with a visual sensory cue in synchronization, stimulating the first processing center,
wherein thesnthat5iDimuiatio of the first processing center and the visual processing center is effective for teaching the user to perform a version of the event.

8. A method according to claim 7: wherein the body member is at least one of a hand and at least one finger of the performer; and wherein the event is piece of music to be performed on a musical instrument, the performance object is the musical instrument and the performance element is at least one of a key, a string and a valve of the musical instrument.

9. A method according to claim 7: wherein the first sensory cue is one of a haptic, auditory and visual sensory cue; and further comprising:
recording, during the performance of the event, at least one of haptic, auditory and visual data related to the performance of the event;
determining at least a second sensory cue dependent on the recorded at least one of haptic, auditory and visual data; and applying, during the learning session, the at least said second sensory cue synchronized with the application of the that sensory cue effective for stimulating at least a second processing center of the brain of the user.

10. A method according to claim 7: wherein the applied electrical signal causes a sensation or contraction in the muscles of the user.

11. A method according to claim 7: wherein the applied first sensory cue stimulates at least one of nerves and muscles of the user.

12. A method according to claim 7: wherein the applied first sensory cue comprises at least one of a vibration and an electrical signal.

13. A method according to claim 7: wherein the applied first sensory cue comprises an audio sensory cue.

14. A method according to claim 7: further comprising detecting electrical impulses of the user during the learning session.

15. An apparatus, comprising:
at least one processors; and
at least one memory including computer program code, the at least one memory and the computer program code configured to, with the at least one processor, cause the apparatus to perform at least the following:
receive a recorded signal, the recorded signal being a signal generated for recording during a performance of an event dependent on a detected change in position of a body member of a performer relative to a performance element of a performance object with which the event was performed;
determine the a first sensory cue dependent on the recorded signal;
apply the first sensory cue to indicate to a user during a learning session the change in position of the body member of the performer during the performance of the event, wherein the first sensory cue is one of a haptic, auditory and visual sensory cue effective for stimulating a first processing center of a brain of the user;
receive a visual sensory data;
determine from the received visual sensory data a visual sensory cue capable of being displayed to the user on, a video display device; and
display the visual sensory cue to the user during the learning session wherein the visual sensory cue provides a virtual visual indication to the user of the change in position of the body member of the performer during the performance, the visual sensory cue being effective for stimulating the visual processing center of the brain of the user, the visual sensory cue being synchronized with the first sensory cue so that the chance in position of body member of the performer is virtually indicated in synhronization with the first sensory cue and so that the visual processing center is stimulated with a visual sensor cue in synchronization with a first sensory cue stimulating the first processing center, wherein the synchronization stimulation of the first processing center and the visual processing center is effective for teaching the user to perform a version of the event.

16. An apparatus according to claim 15: wherein the change in position of the body member is detected from electrical impulses received from the body member.

17. An apparatus according to claim 15:
wherein the at least one memory and the computer program code are configured to, with the at least one processor, cause the apparatus at least to further:
receive at least one of haptic, auditory and visual data related to the performance of the event;

determine at least a second sensory cue dependent on the at least one of haptic, auditory and visual data; and apply, during the learning session, the at least said second sensory cue synchronized with the application of the first sensory cue effective for stimulating at least a second processing center of the brain of the user.

18. A method according to claim 17: wherein the applied first sensory cue stimulates at least one of nerves and muscles of the user, and wherein the applied second sensory cue comprises an audio sensory cue.

19. An apparatus according to claim 15: wherein the body member is at least one finger of the performer, the event is piece of music to be performed on a musical instrument, the performance object is the musical instrument and the performance element is at least one of a key, a string and a valve of the musical instrument; and wherein the at least one memory and the computer program code are configured to, with the at least one processor, cause the apparatus at least to further:

provide auditory information to the user in the form of at least one note corresponding to a musical tone played on the musical instrument, said musical tone being a member of a plurality of musical tones played in series and making up the piece of music performed by the performer;

provide the first sensory cue as haptic information corresponding to the change in position of the at least one finger of the performer, the haptic information being applied to a corresponding at least one finger of the user, the haptic information being synchronized to the auditory information so that said at least one finger of the user is stimulated at the same time the musical tone is heard by the user; and provide visual information corresponding to said at least one note, the visual information being synchronized to the auditory information so that the user sees the visual information at the same time said at least one finger is stimulated when said at least one note is heard by the user so that the user is contemporaneously stimulated with an auditory cue, a haptic cue and a visual cue indicating the at least one musical note to be played on a musical instrument when learning the plurality of musical tones played in series and making up the piece of music played by the performer on the musical instrument.

20. An apparatus according to claim 15: wherein the at least one memory and the computer program code configured to, with the at least one processor, cause the apparatus to further perform; detecting electrical impulses of the use.

* * * * *